US010106858B2

(12) United States Patent
Maurin et al.

(10) Patent No.: US 10,106,858 B2
(45) Date of Patent: Oct. 23, 2018

(54) **METHOD FOR THE IN VITRO DETECTION OF STRAINS OF *LEGIONELLA PNEUMOPHILA* RESISTANT TO ANTIBIOTICS**

(71) Applicants: UNIVERSITE JOSEPH FOURIER, Grenoble (FR); CENTRE HOSPITALIER UNIVERSITAIRE DE GRENOBLE, Grenoble (FR)

(72) Inventors: Max Maurice Louis Maurin, Meylan (FR); Dominique Schneider, Saint-Martin D'Heres (FR); Lubana Shadoud, La Tronche (FR); Sophie Jarraud, Lyons (FR); Jean Francois Timsit, Grenoble (FR); Jerome Etienne, Caluire (FR)

(73) Assignees: UNIVERSITE GRENOBLE ALPES, Saint Martin d'Heres (FR); CENTRE HOSPITALIER UNIVERSITAIRE GRENOBLE ALPES, Grenoble (FR)

(*) Notice: Subject to any disclaimer, the term of this patent is extended or adjusted under 35 U.S.C. 154(b) by 153 days.

(21) Appl. No.: 14/900,626

(22) PCT Filed: Jun. 17, 2014

(86) PCT No.: PCT/FR2014/051488
§ 371 (c)(1),
(2) Date: Dec. 22, 2015

(87) PCT Pub. No.: WO2014/207347
PCT Pub. Date: Dec. 31, 2014

(65) Prior Publication Data

US 2016/0208316 A1 Jul. 21, 2016

(30) Foreign Application Priority Data

Jun. 27, 2013 (FR) ..................................... 13 56225

(51) Int. Cl.
*C12Q 1/689* (2018.01)
*C12Q 1/6806* (2018.01)

(52) U.S. Cl.
CPC ........... *C12Q 1/689* (2013.01); *C12Q 1/6806* (2013.01); *C12Q 2600/106* (2013.01); *C12Q 2600/156* (2013.01); *C12Q 2600/16* (2013.01); *Y02A 50/451* (2018.01)

(58) Field of Classification Search
None
See application file for complete search history.

(56) References Cited

FOREIGN PATENT DOCUMENTS

| | | |
|---|---|---|
| WO | 01-23604 | 4/2001 |
| WO | 2014-207347 | 12/2014 |

OTHER PUBLICATIONS

Jonas et al. (Development and mechanism of fluoroquinolone resistance in Legionella pneumophila, J Antimicrob Chemother. Feb. 2003;51(2):275-80) (Year: 2003).*
Almahmoud et al. (Mutational paths towards increased fluoroquinolone resistance in Legionella pneumophila, J Antimicrob Chemother. Aug. 2009;64(2):284-93. Epub May 27, 2009) (Year: 2009).*
Maurin et al. (Real-time PCR as a Diagnostic Tool for Bacterial Diseases, Expert Rev Mol Diagn. Sep. 2012;12(7):731-54) (Year: 2012).*
International search report, dated Nov. 29, 2014; Application No. PCT/FR2014/051488.
Almahmoud et al., "Mutational paths towards increased fluoroquinolone resistance in Legionella pneumophila," Journal of Antimicrobial Chemotherapy, vol. 64, No. 2, May 27, 2009, pp. 284-293.
Database Biosis, Biosciences Information Service, 2002; Linde et al., "The amino acid substituion Asp87Tyr in GyrA of Legionella pneumophila Sgl is associated with elevated MICs to nalidixic acid but not to ciprofloxacin or moxifloxacin in vitro,"; Abstracts of the Interscience Conference on Microbial Agents and Chemotherapy.
Feddersen et al., "GryA sequence-based typing of Legionella," Medical Microbiology and Immunology, vol. 189, No. 1, Sep. 5, 2000.
Glocker et al., "Rapid Detection of Point Mutations in the gryA Gene of Helicobacter pylori Conferring Resistance to Ciprofloxacin by a Fluorescence Resonance Energy Transfer-Based Real-Time PCR Approach," Journal of Clinical Microbiology, vol. 42, No. 5, May 1, 2004, pp. 2241-2246.
Jonas et al., "Development and mechanism of fluoroquinolone resistance in Legionella pneumophila," Journal of Antimicrobial Chemotherapy, vol. 51, No. 2, Jan. 6, 2003, pp. 275-280.
Walker et al., "Use of a LightCycler gryA Mutation Assay for Rapid Identification of Mutations Conferring Decreased Susceptability to Ciprofloxacin in Multiresistant *Salmonella enterica* Serotype Typhimurium DT104 Isolates," Journal of Clinical Microbiology, vol. 39, No. 4, Apr. 1, 2001, pp. 1443-1448.

* cited by examiner

*Primary Examiner* — Aaron A Priest
(74) *Attorney, Agent, or Firm* — Young & Thompson

(57) ABSTRACT

Disclosed is a method for the in vitro detection of strains of *Legionella pneumophila*, resistant to antibiotics, in particular to the fluoroquinolones. Also disclosed are nucleotide probes and a kit of reagents allowing the detection of *Legionella pneumophila* bacterial strains that are resistant to antibiotics, in particular of the fluoroquinolone type.

22 Claims, 7 Drawing Sheets

Specification includes a Sequence Listing.

Melting peaks

Amplification curves

Melting point curves

Melting point curves

Melting point curves

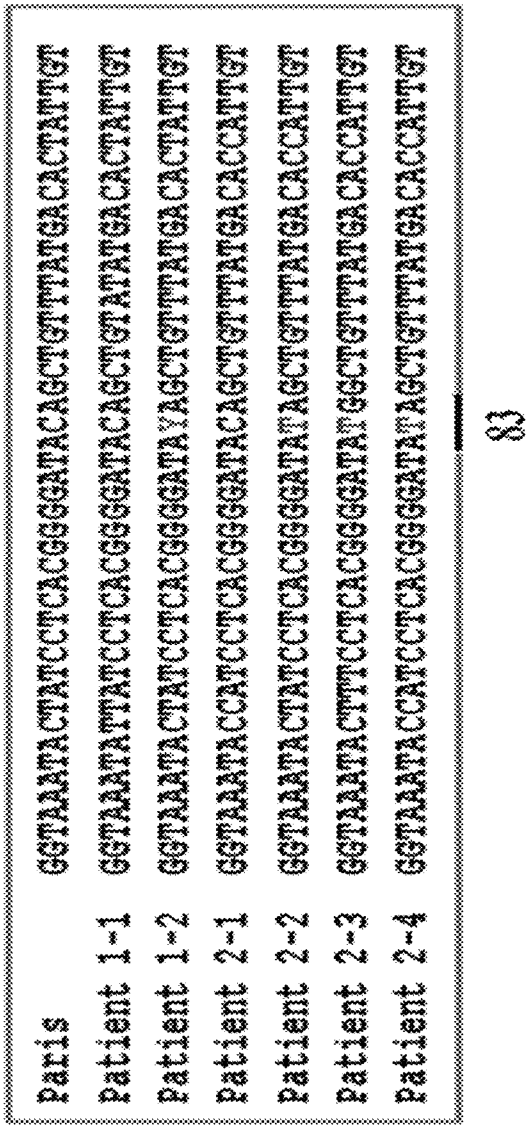

FIGURE 6

| | |
|---|---|
| Paris | GGTAAATACTTATCCTCACGGGGATACAGCTGTTTATGACACTATTGT |
| Patient 1-1 | GGTAAATATTATCCTCACGGGGATACAGCTGTATATGACACTATTGT |
| Patient 1-2 | GGTAAATACTATCCTCACGGGGATAYAGCTGTTTATGACACTATTGT |
| Patient 2-1 | GGTAAATACCATCCTCACGGGGATACAGCTGTTTATGACACTATTGT |
| Patient 2-2 | GGTAAATACTTATCCTCACGGGGATATAGCTGTTTATGACACCATTGT |
| Patient 2-3 | GGTAAATACTTTCCTCACGGGGATANGGCTGTGTTATGACACCATTGT |
| Patient 2-4 | GGTAAATACCATCCTCACGGGGATANAGCTGTTTATGACACCATTGT |

METHOD FOR THE IN VITRO DETECTION OF STRAINS OF *LEGIONELLA PNEUMOPHILA* RESISTANT TO ANTIBIOTICS

FIELD OF THE INVENTION

The present invention relates to a method for the in vitro detection of strains of *Legionella pneumophila* that are resistant to antibiotics, in particular to the fluoroquinolones. The invention also relates to nucleotide probes and a kit of reagents allowing the detection of *Legionella pneumophila* bacterial strains that are resistant to antibiotics, in particular of the fluoroquinolone type.

The invention finally relates to a real-time PCR technique for implementing the abovementioned method for the in vitro detection of antibiotic-resistant strains of *Legionella pneumophila.*

BACKGROUND OF THE INVENTION

*Legionella pneumophila*, a Gram-negative bacterium, is the main etiological agent of legionnaires' disease, a pneumonia potentially serious in humans. The fluoroquinolones and the macrolides are first-line antibiotics in the treatment of legionnaires' disease. However, therapeutic failures are frequent and mortality remains high, on average 10 to 15%, and more than 30% in immunosuppressed patients.

To date, these therapeutic failures have never been associated with acquired antibiotic-resistance in *L. pneumophila*. In fact, numerous studies carried out in vitro have not made it possible to show acquired resistance to fluoroquinolones or macrolides in the natural strains of *L. pneumophila* isolated in humans or isolated from the environment (Baltch A L et al., *Antimicrob. Agents Chemother.,* 1998, 42(12): 3153-6; Baltch A L et al., *Antimicrob. Agents Chemother.,* 1995, 39(8):1661-6; Garcia M T et al., *Antimicrob. Agents Chemother.,* 2000; 44(8): 2176-8; Higa F. et al., *J. Antimicrob. Chemother.* 2005; 56(6):1053-7; Jonas D. et al., *J. Antimicrob. Chemother.,* 2001; 47(2):147-52; Onody C. et al., *J. Antimicrob. Chemother.,* 1997; 39(6):815-6).

Several authors consider that the acquisition of resistance to antibiotics, in particular to the fluoroquinolones, in *L. pneumophila* is a non-existent phenomenon (Roig J. and Rello J., *J. Antimicrob. Chemother.,* 2003; 51(5):1119-29 and Fields B S. et al., *Clin. Microbiol. Rev.* 2002; 15(3): 506-26).

The macrolides and fluoroquinolones are therefore considered as reliable antibiotics in the treatment of legionnaires' disease (Roig J. and Rello *J., J. Antimicrob. Chemother.,* 2003; 51(5):1119-29 and Fields B S. et al., *Clin. Microbiol. Rev.* 2002; 15(3): 506-26).

Only rifampicin is advised against in monotherapy due to the very high risk of selecting resistant mutants in most bacteria.

The fluoroquinolones, broad-spectrum antibiotics, form part of the large family of the quinolones, synthetic antibiotics. The fluoroquinolones are so-called second-generation quinolones, in which fluorine has been added in order to increase the penetration of the molecules of quinolones into the cells (up to 200 times greater). The quinolones and fluoroquinolones target type II bacterial topoisomerases: the DNA gyrase constituted by the GyrA and GyrB proteins, and topoisomerase IV constituted by the parC and parE proteins. Certain mutations affecting the genes encoding these type II topoisomerases are known to induce resistance to the quinolones and fluoroquinolones in the bacteria. In Gram-negative species, in particular in *Escherichia coli*, these fluoroquinolone-resistance mutations mainly affect the gyrA gene encoding the GyrA protein of the DNA gyrase. The substitutions of amino acids which result therefrom are situated in the QRDR region (Quinolone Resistance Determining Region) of GyrA, comprising the amino acids at position 67 to 106 [Soussy C. J. Quinolones and gram-negative bacteria. In Antibiogram. Courvalin P, Leclercq R, and Rice L. B. Eds. ESKA Publishing, ASM Press, 2010, p261-274]. The level of sensitivity to the fluoroquinolones varies in the same bacterium depending on the amino acid or acids situated at these positions. However, the most frequent mutations responsible for fluoroquinolone resistance are those leading to a substitution at the amino acids at positions 83, 87 or more rarely 84 of the GyrA protein (according to the numbering adopted in the case of *Escherichia coli*), constituting DNA gyrase subunit A. The mutations gyrA83 and gyrA87 are frequently observed in vivo [Jacoby G A. Mechanisms of resistance to quinolones. *Clin Infect Dis.* 2005; 41 Suppl 2:S120-6], and have been reproduced in vitro [Barnard F M, Maxwell A. Interaction between DNA gyrase and quinolones: effects of alanine mutations at GyrA subunit residues Ser(83) and Asp(87). Antimicrob Agents Chemother. 2001; 45(7):1994-2000]. These positions are identical on the gyrA gene of *L. pneumophila* strain Paris (NC 006368.1). The inventors have previously shown [Almahmoud I, Kay E, Schneider D, Maurin M. Mutational paths towards increased fluoroquinolone resistance in *Legionella pneumophila. J Antimicrob Chemother.* 2009; 64(2): 284-93] by in vitro selection of fluoroquinolone-resistant mutants, that the key positions for fluoroquinolone resistance in *L. pneumophila* strain Paris also correspond to amino acids 83 and 87 of the GyrA protein.

The strain Paris of *L. pneumophila* (CIP 107629T) is one of the reference strains known to be sensitive to the fluoroquinolones [Roch N, Maurin M. Antibiotic susceptibilities of *Legionella pneumophila* strain Paris in THP-1 cells as determined by real-time PCR assay. *J Antimicrob Chemother.* 2005; 55(6):866-71]. Other strains sensitive to fluoroquinolones are described, such as *L. pneumophila* Philadelphia (ATCC 33152), *L. pneumophila* Lens (CIP 108286) and *L. pneumophila* Lorraine (CIP 108729).

Moreover, the inventors have already described fluoroquinolone-resistant mutant strains selected beforehand in vitro and having one or more of the gyrA83 and gyrA87 mutations [Almahmoud I, Kay E, Schneider D, Maurin M. Mutational paths towards increased fluoroquinolone resistance in *Legionella pneumophila. J Antimicrob Chemother.* 2009; 64(2):284-93]. These are *L. pneumophila* 1 LPPI1 (CIP107629T, namely the strain Paris mutated at position 83 (T83I) of the gyrA gene), *L. pneumophila* 1 LPPI4 (CIP107629T, namely the strain Paris mutated at position 83 (T83I) and at position 87 (D87N) of the gyrA gene) and the strain *L. pneumophila* 1 LPPI5 (CIP107629T, namely the strain Paris mutated at position 83 (T83I) and at position 87 (D87H) of the gyrA gene).

However, it is currently accepted by the scientific community that *L. pneumophila* cannot acquire resistance to antibiotics, in particular to the fluoroquinolones used in clinical practice, in vivo. Several factors are usually mentioned in order to explain this finding in *L. pneumophila* (Fields B S. et al., *Clin Microbiol Rev.* 2002; 15(3):506-26):

1) Unlike *E. coli, L. pneumophila* essentially multiplies in intracellular medium in the free-living protozoans (amoebas) in the aquatic environment or in the alveolar macrophages in the infected patients; this specific multiplication niche would not be suitable for exchanges of antibiotic-resistance genes as has been described in the case of numerous other bacteria (enterobacteria for example);

2) Unlike certain strains of *E. coli*, and in particular entero-haemorrhagic *E. coli*, which have an animal reservoir in ruminants, there is no known animal reservoir for *L. pneumophila*. There would therefore be no pressure of selection by the antibiotics used in veterinary practice or in the agri-food sector;
3) Unlike certain strains of *E. coli* for which cases of interhuman transmission, in particular by faecal-oral transmission, have been reported, legionnaires' disease is not a disease of interhuman transmission, which would also limit the likelihood of transmission of any antibiotic-resistant mutants.

The sensitivity of the bacteria to the antibiotics can be assessed by phenotypic methods, such as the production of an antibiogram and the determination of the minimum inhibitory concentrations (MICs) of the antibiotics. These methods are not carried out routinely for bacteria with fastidious growth requirements such as *L. pneumophila*, due to the impossibility of isolating the bacterial strain in question in most infected patients. In the last few years, molecular methods based on the PCR and real-time PCR techniques have been developed in order to detect the antibiotic resistance mutations on the basis of isolated strains or directly in specimens (clinical or from various environments) containing the mutant strains.

All of the data currently available indicate the non-existence in vivo of antibiotic-resistant strains of *L. pneumophila* in patients suffering from legionnaires' disease and treated with these antibiotics.

Unlike the hypotheses formulated by the scientific community, the Inventors have demonstrated that the acquisition of fluoroquinolone resistance in *L. pneumophila* is possible in vivo, in patients infected with this pathogen.

SUMMARY OF THE INVENTION

One of the aspects of the invention is a method for detecting antibiotic-resistant strains of *L. pneumophila*.

One of the other aspects of the invention is the development of nucleotide sequences of primers and probes (probes in tandem) making it possible to amplify and specifically detect the mutations involved in antibiotic resistance in the species *L. pneumophila*.

One of the other aspects of the invention is a real-time PCR technique making it possible to determine specific mutations responsible for resistance.

One of the other aspects of the invention is a kit for detecting the fluoroquinolone resistance of the *L. pneumophila* strains, making it possible to avoid therapeutic failures and high mortality in patients suffering from legionnaires' disease.

BRIEF DESCRIPTION OF THE DRAWINGS

FIG. 6 shows the results of sequencing of the gyrA gene for the *L. pneumophila* strain Paris which is sensitive to the fluoroquinolones, and for the respiratory specimens taken from patients 1 and 2, either before treatment with the fluoroquinolones (1-1 and 2-1) or at different times during treatment with these antibiotics (1-2, 2-2, 2-3, and 2-4).

DETAILED DESCRIPTION OF THE INVENTION

Figure 1:
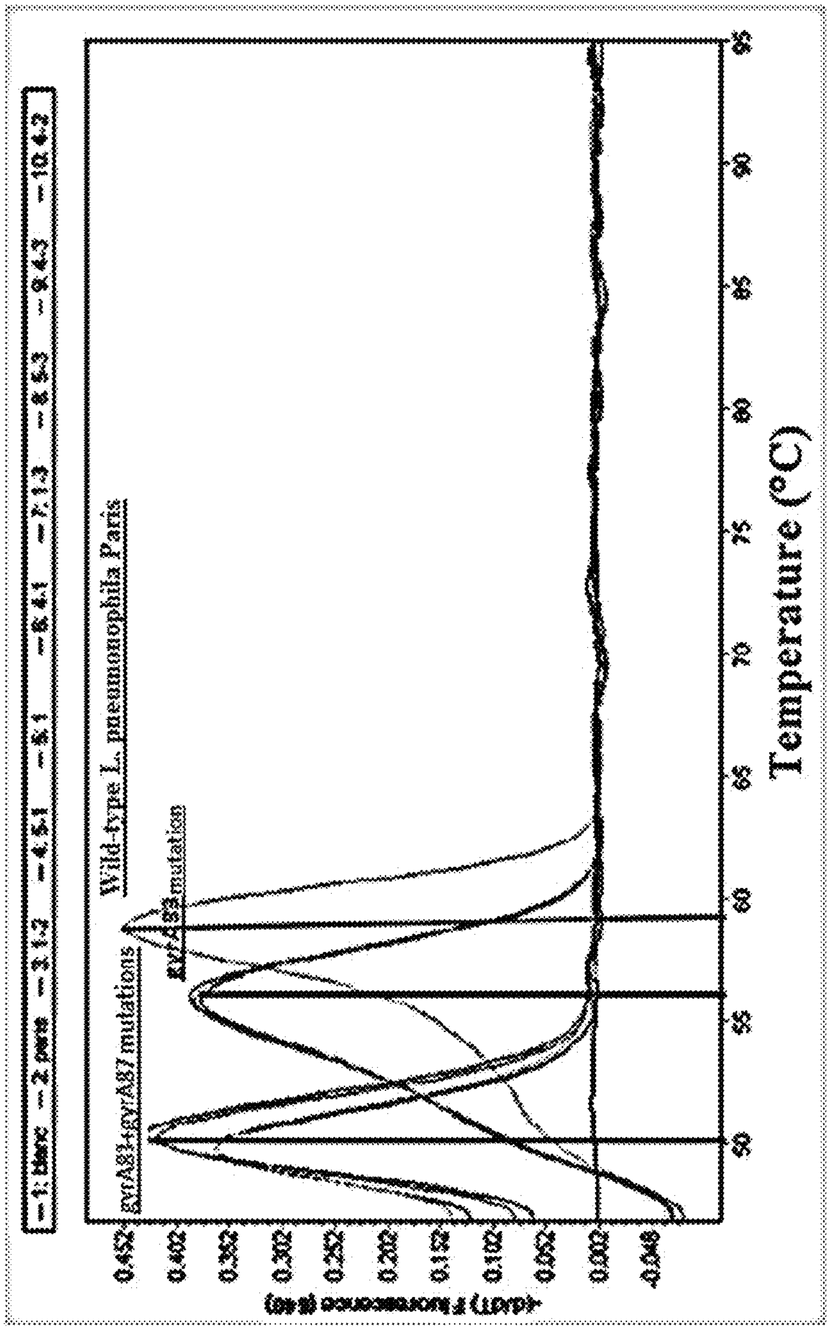
FIG. 1 shows the melting point curves obtained for an *L. pneumophila* strain Paris that is sensitive to the fluoroquinolones (melting point 59° C.), for a mutant gyrA83 (melting point 56.6° C.) and for a double mutant gyrA83+gyrA87 (melting point 50° C.)

The present invention is based on an in vitro method allowing the demonstration of at least one bacterial strain of *Legionella pneumophila* that is resistant to antibiotics, in particular of the fluoroquinolone type, in a biological sample, by detecting:

- a mutation on at least one of positions 83, 84, 87 or equivalents with respect to SEQ ID NO: 1 in a GyrA protein of *L. pneumophila* having at least 90% identity with SEQ ID NO: 1, said mutation resulting in a mutated GyrA protein, or
- a nucleic acid encoding said mutated GyrA protein, the detection of said mutation or of the nucleic acid encoding said mutated GyrA protein indicating the presence of at least one antibiotic-resistant bacterial strain of *Legionella pneumophila*, in the sample.

SEQ ID NO: 1 shows the sequence of the wild-type GyrA protein of L. *Pneumophila* (GyrA protein of *L. pneumophila* strain Paris, accession number: YP 123696.1), encoded by nucleotide sequence SEQ ID NO: 13.

By biological sample is meant, any specimen taken from tissues, cells, organs, fluids, secretions or blood, originating from the human or animal body, and derivatives thereof.

Within the meaning of the present application, antibiotic resistance is defined as the ability of a microorganism to resist the effects of the antibiotics, in vitro and in vivo.

This resistance is usually defined by measuring the minimum inhibitory concentration (MIC) of an antibiotic vis-à-vis a given bacterium, according to a method validated by a reference body, such as the European Committee on Antimicrobial Susceptibility Testing (EUCAST) in Europe [E. Matuschek, D. F. J. Brown and G. Kahlmeter. Development of the EUCAST disk diffusion antimicrobial susceptibility testing method and its implementation in routine microbiology laboratories. *Clin Microbiol Infect* 2014; 20: 0255-0266], or the Clinical and Laboratory standard Institute (CLSI) in the United States [CLSI. M07-A9: Methods for Dilution Antimicrobial Susceptibility Tests for Bacteria That Grow Aerobically; Approved Standard—Ninth Edition. Vol. 32 No 2]. A strain is said to be resistant to an antibiotic if the MIC of this antibiotic vis-à-vis the strain considered is greater than a critical value defined by this same reference body.

Within the meaning of the present Application, the term "equivalent position" means a nucleotide of the gyrA gene or an amino acid of the GyrA protein of the same nature and function as that described in *E. coli* for a given position, although the numbering of this position can be different in the species considered with respect to *E. coli* due to a different number of nucleotides (gyrA) or of amino acids (GyrA) between the two species. By "identity", is also meant the number of identical nucleotides between two sequences of the same length, determined for each position in the sequences.

In the wild-type strains of *L. pneumophila*, position 83 of the GyrA protein is occupied by a threonine (T), position 84 is occupied by an alanine (A) and position 87 is occupied by an aspartic acid (D).

A bacterial strain of *L. pneumophila* according to the invention, is referred to as mutated when position 83 of the GyrA protein is no longer occupied by a threonine (T), and/or when position 84 is no longer occupied by an alanine (A), and/or when as position 87 is no longer occupied by an aspartic acid (D).

A particular embodiment of the invention relates to an in vitro method allowing the demonstration of at least one bacterial strain of *Legionella pneumophila* that is resistant to antibiotics, in particular of the fluoroquinolone type, in a biological sample, a method in which the mutated GyrA protein is such that:

- the amino acid at position 83 is different from T and the amino acids at positions 84 and 87 can correspond to any amino acid, or
- said amino acid at position 84 is different from A, and the amino acids at positions 83 and 87 can correspond to any amino acid, or
- said amino acid at position 87 is different from D, and the amino acids at positions 83 and 84 can correspond to any amino acid.

The expression "the amino acids at positions 84 and 87 (or 83 and 87) or (83 and 84) can correspond to any amino acid" means that said amino acids can equally well be the amino acid present in a wild-type strain as any other amino acid. In the latter case, the amino acid considered therefore constitutes a mutation.

A bacterial strain of *L. pneumophila* according to the invention having a mutated GyrA protein, can therefore contain a single mutation, a double mutation or a triple mutation.

The strains comprising a single mutation are therefore mutated at position 83 or at position 84 or at position 87. The strains comprising a double mutation are therefore mutated either at positions 83 and 84, or at positions 84 and 87, or at positions 83 and 87.

The strains comprising a triple mutation are therefore mutated at the three positions 83; 84 and 87 concomitantly.

According to another embodiment of the invention, the in vitro method allowing the demonstration of at least one bacterial strain of *Legionella pneumophila* that is resistant to antibiotics, in particular of the fluoroquinolone type, is applied when the mutated GyrA protein is such that:

- said amino acid at position 83 is: I, L, W, A or V and the amino acids at positions 84 and 87 can correspond to any amino acid, or
- said amino acid at position 84 is: P or V and the amino acids at positions 83 and 87 can correspond to any amino acid, or
- said amino acid at position 87 is: N, G, Y, H or V and the amino acids at positions 83 and 84 can correspond to any amino acid, or
- said amino acid at position 83 is: I, L, W, A or V, said amino acid at position 84 is: P or V, and said amino acid at position 87 is any amino acid, or
- said amino acid at position 83 is: I, L, W, A or V, said amino acid at position 87 is: N, G, Y, H or V and said amino acid at position 84 is any amino acid, or
- said amino acid at position 84 is: P and V, said amino acid at position 87 is: N, G, Y, H or V and said amino acid at position 83 is any amino acid, or
- said amino acid at position 83 is: I, L, W, A or V, said amino acid at position 84 is: P or V and said amino acid at position 87 is: N, G, Y, H or V.

When the amino acid at position 83 is mutated, the amino acids at position 84 and 87 can be the amino acids of the wild-type protein, i.e. A (alanine) and D (aspartic acid) respectively or any other amino acid, i.e. the amino acids at position 84 and 87 can also be mutated.

When the amino acid at position 84 is mutated, the amino acids at position 83 and 87 can be the amino acids of the wild-type protein, i.e. T (threonine) and D (aspartic acid) respectively or any other amino acid, i.e. the amino acids at position 83 and 87 can also be mutated.

When the amino acid at position 87 is mutated, the amino acids at position 83 and 84 can be the amino acids of the wild-type protein, i.e. T (Threonine) and A (Alanine) respectively or any other amino acid, i.e. the amino acids at position 83 and 84 can also be mutated.

According to another advantageous embodiment of the invention, said in vitro method allowing the demonstration of at least one bacterial strain of *Legionella pneumophila* that is resistant to antibiotics, in particular of the fluoroquinolone type, is applied when the mutated GyrA protein is such that:

- said amino acid at position 83 is: an isoleucine (I), a leucine (L), a tryptophane (W), an alanine (A) or a valine (V), said amino acid at position 84 is an alanine (A) and said amino acid at position 87 is an aspartic acid (D), or
- said amino acid at position 84 is: a proline (P) or a valine (V) and said amino acid at position 83 is a threonine (T) and said amino acid at position 87 is an aspartic acid (D), or
- said amino acid at position 87 is: an asparagine (N), a glycine (G), a tyrosine (Y), a histidine (H) or a valine (V) and said amino acid at position 83 is a threonine (T) and said amino acid at position 84 is an alanine (A), or
- said amino acid at position 83 is: an isoleucine (I), a leucine (L), a tryptophane (W), an alanine (A) or a valine (V), said amino acid at position 84 is: a proline (P) or a valine (V) and said amino acid at position 87 is an aspartic acid (D), or
- said amino acid at position 83 is: an isoleucine (I), a leucine (L), a tryptophane (W), an alanine (A) or a valine (V), said amino acid at position 87 is: an asparagine (N), a glycine (G), a tyrosine (Y), a histidine (H) or a valine (V) and said amino acid at position 84 is an alanine (A), or
- said amino acid at position 84 is: a proline (P) or a valine (V), said amino acid at position 87 is: an asparagine (N), a glycine (G), a tyrosine (Y), a histidine (H) or a valine (V) and said amino acid at position 83 is a threonine (T).

The table below shows all of the possible amino-acid mutations, at each of the three positions 83, 84 and 87 and the corresponding codons.

| Amino acid at position 83 | | Amino acid at position 84 | | Amino acid at position 87 | |
|---|---|---|---|---|---|
| I | ATT | P | CCT | N | AAT |
| | ATC | | CCC | | AAC |
| | ATA | | CCA | | |
| | | | CCG | | |
| L | CTT | V | GTT | G | GGT |
| | CTC | | GTC | | GGC |
| | CTA | | GTA | | GGA |
| | CTG | | GTG | | GGG |
| | TTG | | | | |
| | TTA | | | | |
| W | TGG | | | Y | TAT |
| | | | | | TAC |
| A | GCT | | | H | CAT |
| | GCC | | | | CAC |
| | GCA | | | | |
| | GCG | | | | |
| V | GTT | | | V | GTT |
| | GTC | | | | GTC |
| | GTA | | | | GTA |
| | GTG | | | | GTG |

The method according to the invention allows the detection of a mutated GyrA protein which comprises the following consensus sequence:

(SEQ ID NO: 2)
$GDX_1X_2VYX_3T$, in which: $X_1$, $X_2$ and $X_3$ correspond to the amino acids mutated at positions 83, 84 and 87 respectively, and

- $X_1$ is different from T (threonine), and $X_2$ and $X_3$ are any amino acid, or
- $X_2$ is different from A (alanine), and $X_1$ and $X_3$ are any amino acid, or
- $X_3$ is different from D (aspartic acid), and $X_1$ and $X_2$ are any amino acid.

According to a particular embodiment of the present invention, in the mutated GyrA protein, the amino acid corresponding to $X_1$, different from T, can be an isoleucine (I), a leucine (L), a tryptophane (W), an alanine (A) or a valine (V), and $X_2$ and $X_3$ correspond to any amino acid, or

- the amino acid corresponding to $X_2$ is a proline (P) or a valine (V), and $X_1$ and $X_3$ correspond to any amino acid, or
- the amino acid corresponding to $X_3$ is an asparagine (N), a glycine (G), a tyrosine (Y), a histidine (H) or a valine (V), and $X_1$ and $X_2$ correspond to any amino acid, or
- the amino acid corresponding to $X_1$, different from T, is an isoleucine (I), a leucine (L), a tryptophane (W), an alanine (A) or a valine (V), $X_2$ is a proline (P) or a valine (V) and $X_3$ is any amino acid, or
- the amino acid corresponding to $X_1$, different from T, is an isoleucine (I), a leucine (L), a tryptophane (W), an alanine (A) or a valine (V), $X_3$ is an asparagine (N), a glycine (G), a tyrosine (Y), a histidine (H) or a valine (V) and $X_2$ is any amino acid, or
- the amino acid corresponding to $X_2$ is a proline (P) or a valine (V), $X_3$ is an asparagine (N), a glycine (G), a tyrosine (Y), a histidine (H) or a valine (V) and $X_1$ is any amino acid, or
- the amino acid corresponding to $X_1$, different from T, is an isoleucine (I), a leucine (L), a tryptophane (W), an alanine (A) or a valine (V), $X_2$ is a proline (P) or a valine (V) and $X_3$ is an asparagine (N), a glycine (G), a tyrosine (Y), a histidine (H) or a valine (V).

According to a particular embodiment of the present invention, the method of the invention allows the detection of a mutated GyrA protein which comprises the consensus sequence $GDX_1X_2VYX_3T$ in which:

- $X_1$ is I, L, W, A or V, $X_2$ is A and $X_3$ is D, or
- $X_2$ is P or V, $X_1$ is T and $X_3$ is D, or
- $X_3$ is N, G, Y, H or V, $X_1$ is T and $X_2$ is A, or
- $X_1$ is I, L, W, A or V, $X_2$ is P or V and $X_3$ is D, or
- $X_1$ is I, L, W, A or V, $X_3$ is N, G, Y, H or V and $X_2$ is A, or
- $X_2$ is P or V, $X_3$ is N, G, Y, H or V and $X_1$ is T, or
- $X_1$ is I, L, W, A or V, $X_2$ is P or V and $X_3$ is N, G, Y, H or V.

According to a particular embodiment of the present invention, the method allows the detection of the sequence of the gene encoding said mutated GyrA protein. This sequence has at least one nucleotide substitution with respect to SEQ ID NO: 3 (GGGGATACAGCTGTTTATGACAC), at a position equivalent to position 7, 8, 10, 11, 19, 20 or 21 with respect to SEQ ID NO: 3, where the nucleotides at positions 7 and 8 correspond to the first two nucleotides of the codon encoding the amino acid at position 83 of the GyrA protein of *Legionella pneumophila*, the nucleotides at positions 10 and 11 correspond to the first two nucleotides of the codon encoding the amino acid at position 84, and the nucleotides at positions 19, 20 and 21 correspond to the three nucleotides of the codon encoding the amino acid at position 87.

According to another embodiment of the present invention, the sequence of the nucleic acid encoding said mutated GyrA protein comprises a sequence chosen from:

SEQ ID NO: 4
(GGGGATTCAGCTGTTTATGACAC),

SEQ ID NO: 5
(GGGGATCCAGCTGTTTATGACAC),

SEQ ID NO: 6
(GGGGATGCAGCTGTTTATGACAC),

SEQ ID NO: 7
(GGGGATAAAGCTGTTTATGACAC),

SEQ ID NO: 8
(GGGGATATAGCTGTTTATGACAC),

SEQ ID NO: 9
(GGGGATAGAGCTGTTTATGACAC),

SEQ ID NO: 10
(GGGGATACAACTGTTTATGACAC),

SEQ ID NO: 11
(GGGGATACATCTGTTTATGACAC),

SEQ ID NO: 12
(GGGGATACACCTGTTTATGACAC),

SEQ ID NO: 14
(GGGGATACAGATGTTTATGACAC),

SEQ ID NO: 15
(GGGGATACAGTTGTTTATGACAC),

SEQ ID NO: 16
(GGGGATACAGGTGTTTATGACAC),

SEQ ID NO: 17
(GGGGATACAGCTGTTTATAACAC),

-continued

SEQ ID NO: 18
(GGGGATACAGCTGTTTATTACAC),

SEQ ID NO: 19
(GGGGATACAGCTGTTTATCACAC),

SEQ ID NO: 20
(GGGGATACAGCTGTTTATGTCAC),

SEQ ID NO: 21
(GGGGATACAGCTGTTTATGGCAC),

SEQ ID NO: 22
(GGGGATACAGCTGTTTATGCCAC),

SEQ ID NO: 23
(GGGGATACAGCTGTTTATGAGAC),

SEQ ID NO: 24
(GGGGATACAGCTGTTTATGAAAC),

SEQ ID NO: 25
(GGGGATTTAGCTGTTTATGACAC),

SEQ ID NO: 26
(GGGGATTTGGCTGTTTATGACAC),

SEQ ID NO: 27
(GGGGATCTTGCTGTTTATGACAC),

SEQ ID NO: 28
(GGGGATCTCGCTGTTTATGACAC),

SEQ ID NO: 29
(GGGGATCTAGCTGTTTATGACAC),

SEQ ID NO: 30
(GGGGATCTGGCTGTTTATGACAC),

SEQ ID NO: 31
(GGGGATTGGGCTGTTTATGACAC),

SEQ ID NO: 32
(GGGGATGCTGCTGTTTATGACAC),

SEQ ID NO: 33
(GGGGATGCCGCTGTTTATGACAC),

SEQ ID NO: 34
(GGGGATGCGGCTGTTTATGACAC),

SEQ ID NO: 35
(GGGGATGTTGCTGTTTATGACAC),

SEQ ID NO: 36
(GGGGATGTCGCTGTTTATGACAC),

SEQ ID NO: 37
(GGGGATGTAGCTGTTTATGACAC),

SEQ ID NO: 38
(GGGGATGTGGCTGTTTATGACAC),

SEQ ID NO: 39
(GGGGATACACCCGTTTATGACAC),

SEQ ID NO: 40
(GGGGATACACCAGTTTATGACAC),

SEQ ID NO: 41
(GGGGATACACCGGTTTATGACAC),

SEQ ID NO: 42
(GGGGATACAGTCGTTTATGACAC),

SEQ ID NO: 43
(GGGGATACAGTAGTTTATGACAC),

SEQ ID NO: 44
(GGGGATACAGTGGTTTATGACAC),

-continued

SEQ ID NO: 45
(GGGGATACAGCTGTTTATAATAC),

SEQ ID NO: 46
(GGGGATACAGCTGTTTATGGTAC),

SEQ ID NO: 47
(GGGGATACAGCTGTTTATGGAAC),

SEQ ID NO: 48
(GGGGATACAGCTGTTTATGGGAC),

SEQ ID NO: 49
(GGGGATACAGCTGTTTATTATAC),

SEQ ID NO: 50
(GGGGATACAGCTGTTTATCATAC),

SEQ ID NO: 51
(GGGGATACAGCTGTTTATGTTAC),

SEQ ID NO: 52
(GGGGATACAGCTGTTTATGTAAC),

SEQ ID NO: 53
(GGGGATACAGCTGTTTATGTGAC),

SEQ ID NO: 54
(GGGGATTTCGCTGTTTATGACAC),

SEQ ID NO: 55
(GGGGATATTGCTGTTTATGACAC),

SEQ ID NO: 56
(GGGGATATCGCTGTTTATGACAC),

SEQ ID NO: 61
(GGGGATTTTGCTGTTTATGACAC),

In the context of the present invention, the detection of the presence of said mutated GyrA protein or of the target nucleic acid encoding said mutated GyrA protein, including the detection of the mRNA encoded by the mutated gene, is carried out by a technique chosen from: western blot, northern blot, southern blot, PCR (Polymerase Chain Reaction), real-time PCR, hybridization PCR, array PCR, TMA (Transcription Mediated Amplification), NASBA (Nucleic Acid Sequence Based Amplification), LCR (Ligase Chain Reaction), the DNA/RNA hybridization, DNA chip, DNA/RNA sequencing, dot-blot, the RFLP (Restriction Fragment Length Polymorphism) technique.

In an advantageous embodiment, the detection of the presence of said nucleic acid encoding said mutated GyrA protein is carried out by real-time PCR.

Real-time PCR uses the basic principle of standard PCR (cyclic amplification of a DNA fragment, based on an enzymological reaction) the difference being an amplification measured not at the end but throughout the reaction, therefore in real time.

At each amplification cycle, the quantity of DNA is measured by means of a fluorescent label the emission of which is directly proportional to the quantity of amplicons produced. This makes it possible to obtain reaction kinetics and therefore DNA quantification whereas the standard PCR gives only the final measurement.

The detection or the quantification of the fluorescent signal in real time can be carried out using intercalating agents or probes.

The intercalating agent most used at present is SYBR® Green (Roche, Meylan, France). As regards the probes, there are 4 different technologies, allowing the measurement of a fluorescent signal: “Taqman” or hydrolysis probes, “Hyb- Probe" (FRET) or hybridization of 2 probes, "Molecular Beacons" and "Scorpion" primers.

In the context of the invention, real-time PCR is used for the detection of the gyrA83, 84 and/or 87 mutations, by using for example, two probes in tandem: a so-called anchoring probe and a so-called detection probe. In the context of the present invention, the fluorophore situated on the anchoring probe is for example LCRed-640 (Roche Diagnostic), and the fluorophore situated on the emission probe is for example fluorescein.

The binding of these two probes to the target DNA first leads to the excitation of the fluorophore situated on the anchoring probe, then a FRET "fluorescence resonance energy transfer" phenomenon occurs, between this fluorophore and the fluorescein situated on the detection probe. The fluorescein then emits fluorescence measured in real time by the device, the intensity of which is proportional to the quantity of DNA amplified.

A melting point curve, established at the end of amplification, makes it possible to determine a melting point characteristic of the size and content of amplicon bases (amplified DNA).

A mutation affecting this fragment leads to a downward shift of the melting point. The fragment tested here is delimited from base 241 to base 263 of gyrA of the strain *L. pneumophila* Paris [GGGGATACAGCTGTTTATGACAC] (SEQ ID NO: 3), i.e. from amino acid 81 to amino acid 88 of GyrA of said strain [GDTAVYDT] (SEQ ID NO: 62). It therefore includes the positions T83, A84 and D87, which are linked to fluoroquinolone resistance in *L. pneumophila.*

This technique shows a change in the melting point in case of alteration of this DNA fragment, irrespective of the mutation and its position. Because of natural variations of *L. pneumophila* in the nucleotide sequence, which can lead to other mutations, the results obtained by the method according to the invention can be confirmed by a complementary technique such as for example the sequencing of the amplified DNA.

It is however easy to envisage, from the state of the art, other techniques making it possible to overcome variations of DNA sequences at the anchoring probe and/or to specifically target the mutations of interest without requiring an additional stage.

For example, the use of a detection probe of the hydrolysis probe or "Taqman", "beacon" or "scorpion" type could make it possible to target the same region of gyrA where the mutations responsible for the substitutions at positions 83, 84 and 87 are produced, without the use of an anchoring probe. Examples of this type of technique are presented in the literature, relating to the detection of fluoroquinolone resistance in *Mycobacterium tuberculosis* (Chakravorty S. et al., *J Clin Microbiol.* 2011; 49(3):932-40) or in *Staphylococcus aureus* (Lapierre P. et al., *J Clin Microbiol.* 2003; 41(7):3246-51).

It is also possible to specifically detect expected mutations on specific nucleotides by other techniques so as to eliminate false positive results linked to the mutations not associated with antibiotic resistance. This can be achieved in particular by the use of multiple probes, "in tandem" (Page S. et al., *Antimicrob. Agents Chemother.,* 2008; 52(11): 4155-8 and Glocker E. et al., *J. Clin. Microbiol.* 2004; 42(5): 2241-6), to hydrolysis or "Taqman" (Ben Shabat M. et al., *J. Clin. Microbiol.,* 2010; 48(8):2909-15 and Wilson D L et al., *J. Clin. Microbiol.,* 2000; 38(11):3971-8), of the "locked nucleic acid probe" type (van Doom H R. et al., *Intl. Tuberc. Lung Dis.,* 2008; 12(7):736-42). The PCR-hybridization technique (Cambau E. et al., *PLoS Negl. Trop. Dis.* 2012; 6(7):1739) or the use of DNA microchips (Matsuoka M. et al., *J. Med. Microbiol.* 2008; 57:1213-1219) also allow the specific detection of resistance mutations. These different techniques make it possible to detect SNP (single nucleotide polymorphism) at specific DNA fragments, and would therefore make it possible to detect, in targeted manner, the mutations responsible for fluoroquinolone resistance in *L. pneumophila.* Certain of these techniques are already marketed such as for example the Xpert TB/RIF® test (Cepheid) which detects, using a "Beacon" probe, rifampicin resistance in *Mycobacterium tuberculosis.*

The method for detecting the presence of the target nucleic acid encoding said mutated GyrA protein, according to the invention comprising the steps of:

a) bringing a biological sample likely to contain a target nucleic belonging to an antibiotic-resistant bacterial strain of *Legionella pneumophila*, into contact with a pair of primers capable of hybridizing specifically with said target nucleic acid, and b) when there is PCR amplification of said target nucleic acid, using the pair of primers in order to obtain an amplification product, said amplification product comprising a sequence having at least 90% identity with sequence SEQ ID NO: 3, c) detecting a nucleic acid encoding the mutated GyrA protein, When a nucleic acid encoding said mutated GyrA protein is detected, this indicates the presence of at least one antibiotic-resistant bacterial strain of *Legionella pneumophila* in the sample.

According to the method of the present invention, the amplification product obtained in step b) is an amplicon of 259 nucleotides. This amplicon of 259 nucleotides corresponds to SEQ ID NO: 57 or to any sequence having a percentage identity equal to at least 90% with sequence SEQ ID NO: 57.

By "amplicon" is meant any DNA fragment amplified by PCR, by means of two primers. In a particular embodiment of the invention, step b) of said method for detecting a target nucleic acid encoding said mutated GyrA protein is carried out using a primer having at least 90% identity with sequence SEQ ID NO: 58, and/or a primer having at least 90% identity with sequence SEQ ID NO: 59.

By "primer" is meant a DNA fragment the size of which is generally comprised between 15 nucleotides and 25 nucleotides, capable of hybridizing with a strand of DNA serving as matrix, with a given melting point, so as to allow the duplication of this strand of DNA.

The primers used in the method according to the invention are represented by the sequences SEQ ID NO: 58 (sense primer, named LpgyrALSFw and corresponding to the following nucleic acid sequence: CCTGATGTACGTGATGGTTTAA) and SEQ ID NO: 59 (anti-sense primer, named LpgyrALSRv and corresponding to the following nucleic acid sequence: GCATGGCAGCTGGAGCATCTCC), or any other nucleic acid sequence having at least 90% identity with said sequences SEQ ID NO: 58 and SEQ ID NO: 59.

Furthermore, step b) of said method for detecting a target nucleic acid encoding said mutated GyrA protein, can be carried out using at least one nucleotide probe capable of hybridizing with the target nucleic acid.

In another particular embodiment of the invention, the detection method requires the use of probes.

In the real-time PCR system developed by the inventors, a so-called detection probe and a so-called anchoring probe are necessary.

The detection probe that can be used in the context of the present invention is a nucleic acid sequence represented by sequence SEQ ID NO: 3 or by any other nucleotide sequence having at least 90% identity with sequence SEQ ID NO: 3 (named LpgyrALSP1). This detection probe is covalently bonded to at least one marker molecule allowing its detection by a suitable device.

The marker molecule is chosen from a fluorochrome or a radioactive isotope. A fluorochrome is a chemical substance capable of emitting fluorescent light after excitation. A fluorochrome that is useful in the context of the invention can be chosen from: fluorescein, Cy2, Cy3, Cy5, Cy7, Red613, Red640, Rhodamine, Texas red, TRITC, Alexa Fluorine, this list not being exhaustive. Preferably, the fluorochrome linked to the detection probe in the context of the invention is fluorescein bonded to the 3' end of said probe.

The detection method according to the invention can also comprise an anchoring probe, which, coupled with the detection probe, allows the detection of the amplification product obtained in step b). The anchoring probe according to the invention is a nucleic acid sequence represented by sequence SEQ ID NO: 60 (named LpgyrALSP3) or by any other nucleotide sequence having at least 90% identity with sequence SEQ ID NO: 60.

This anchoring probe is covalently bonded to at least one marker molecule allowing its detection by a suitable device. In the context of the present invention, the 5' end of the anchoring probe is bonded to an acceptor fluorochrome. The acceptor fluorochrome can be chosen from fluorescein, Cy2, Cy3, Cy5, Cy7, Red613, Red640, Rhodamine, Texas red, TRITC, Alexa Fluorine, this list not being exhaustive. More particularly, the acceptor fluorochrome can be the product LightCycler® Red 640 (Roche Diagnostic).

The anchoring probe has at its 3' end, a phosphorylation denoted "P", preventing its elongation by the DNA polymerase. The anchoring probe is therefore present in the form 5'-LCRed640-TTGTTCGTATGGCTCAGCCTTTTTC-P-3' (SEQ ID NO: 60).

The present invention also aims to protect a pair of primers allowing the amplification of a fragment of the gyrA gene of *Legionella pneumophila*, comprising a primer having at least 90% identity with sequence SEQ ID NO: 58 (LpgyrALSFw), and a primer having at least 90% identity with sequence SEQ ID NO: 59 (LpgyrALSRv).

These pairs of primers make it possible to amplify a fragment comprising 259 nucleotides.

The method according to the invention and quite particularly the step of amplification of a fragment of the gyrA gene can be carried out with a sense primer corresponding to sequence SEQ ID NO:58 and an anti-sense primer chosen from all the nucleic acid sequences having at least 90% identity with sequence SEQ ID NO: 59 or with a sense primer corresponding to one of the sequences chosen from the group comprising all the nucleic acid sequences having at least 90% identity with sequence SEQ ID NO: 58 and an anti-sense primer corresponding to sequence SEQ ID NO: 59 or also with a sense primer corresponding to one of the sequences chosen from the group comprising all the nucleic acid sequences having at least 90% identity with sequence SEQ ID NO: 58 and an anti-sense primer corresponding to one of the sequences chosen from the group comprising all the nucleic acid sequences having at least 90% identity with sequence SEQ ID NO: 59. The present invention also aims to protect a kit of reagents allowing the detection of bacterial strains *Legionella pneumophila* that are resistant to antibiotics, in particular of the fluoroquinolone type, comprising at least one pair of primers allowing the amplification of the fragment of interest, namely the amplicon of 259 nucleotides corresponding to sequence SEQ ID NO:59 and at least one probe chosen from those represented by the sequences SEQ ID NO: 3 and SEQ ID NO: 60, that are the detection and anchoring probes.

The detection method according to the invention can be used for diagnosing an infection with a *Legionella pneumophila* bacterium that is resistant to antibiotics, in particular of the fluoroquinolone type, in a patient.

For this, on the basis of a specimen taken from a patient likely to have antibiotic-resistant strains of *L. pneumophila*, the method for detecting the mutated gyrA gene by real-time PCR is implemented. Such a specimen can in particular be a specimen taken from secretions of the respiratory tract, but also blood, serum, plasma, urine, tissue biopsies (examples: pulmonary or pleural biopsies), different puncture fluids (examples: cerebrospinal fluid, joint fluid, pleural fluid) and various suppurations (example: pulmonary abscess).

The detection method according to the invention can be used for determining or predicting the efficacy of a treatment with fluoroquinolones in a patient infected with the *Legionella pneumophila* bacterium.

In fact, when faced with any therapeutic failure in patients suffering from legionnaires' disease, the detection method according to the invention can be implemented in order to ensure that the patient exhibits no resistance to antibiotics of the fluoroquinolone types, so as to modify the treatment schedule if required.

EXAMPLES

Example 1: Amplification of the GGGGATACAGCTGTTTATGACAC Fragment of the gyrA Gene (ID: 3119437) of the *L. pneumophila* Strain PARIS (Genbank NC_006368.1, SEQ ID NO: 13), Fragment Encoding the Amino Acids Linked with Fluoroquinolone Resistance The primers described below make it possible to amplify and detect a fragment of the gyrA gene of *L. pneumophila* (gyrA gene: SEQ ID NO: 1).

```
Sense primer "LpgyrALSFw":
                                        (SEQ ID NO: 58)
5'-CCTGATGTACGTGATGGTTTAA-3'

Anti-sense primer "LpgyrALSRv":
                                        (SEQ ID NO: 59)
5'-GCATGGCAGCTGGAGCATCTCC-3'

Detection probe "LpgyrALSP1":
                                         (SEQ ID NO: 3)
5'-GGGGATACAGCTGTTTATGACAC-Fluo-3'

Anchoring probe "LpgyrALSP3":
                                        (SEQ ID NO: 60)
5'-LCRed640-TTGTTCGTATGGCTCAGCCTTTTTC-P-3'
```

The detection method is based on real-time PCR, using the so-called FRET (Fluorescence Resonance Energy Transfer) technique. In this system, 2 probes are used, one of which bears, at the 3' end, an emitter fluorochrome and the other, at the 5' end, an acceptor fluorochrome. The probes are chosen so as to hybridize with their target sequences while being spaced from 1 to 5 nucleotides apart from each other. When the two probes are separated, the donor fluorochrome only emits fluorescence background noise whereas when they are hybridized with less than 10 nucleotides of distance, the closeness of the two fluorochromes allows the transfer of energy from the donor fluorochrome to the acceptor fluorochrome causing the fluorescent emission of the latter (FRET: Fluorescent Resonance Energy Transfer). The fluorescence acquisition is then measured, which is proportional to the quantity of DNA synthesized, at the time of hybridization.

The anchoring probe contains the fluorophore LCRed-640 (Sigma Aldrich, L'Isle d'Abeau Chesnes 38297 Saint-Quentin Fallavier, France) at the 5' end. The detection probe contains fluorescein at the 3' end. The emission of fluorescence is detected in real time by the amplification device. A melting point curve is established at the end of amplification and makes it possible to determine a melting point characteristic of the size and content of bases of the amplicon. A mutation affecting this fragment results in a downward shift of the melting point. The fragment tested here goes from the nucleotide situated at position 241 to the nucleotide situated at position 263 of gyrA of *L. pneumophila* Paris [GGGGATACAGCTGTTTATGACAC] (SEQ ID NO: 3), i.e. from amino acid 81 to amino acid 88 of GyrA of *L. pneumophila* Paris [GDTAVYDT] (SEQ ID NO: 62). It therefore includes the positions T83, A84 and D87, which are linked to fluoroquinolone resistance in *L. pneumophila.*

The primers used make it possible to obtain an amplicon of 259 bp (SEQ ID No 57).

The amplification is carried out under the conditions below, with a Light-Cycler type device (Roche Diagnostics, Meylan, France).

| MIX | Initial concentration | PCR Volume | Final concentration |
|---|---|---|---|
| Sense primer | 5 pMol/μL | 2 μL | 0.5 pMol/μL |
| Anti-sense primer | 5 pMol/μL | 2 μL | 0.5 pMol/μL |
| Detection probe | 2 pMol/μL | 2 μL | 0.2 pMol/μL |
| Anchoring probe | 2 pMol/μL | 4 μL | 0.4 pMol/μL |
| Mgcl2 | | 2.4 μL | |
| FastStart | | 2 μL | |
| UDG | | 0.5 μL | |
| PCR-grade water | | 0.1 μL | |
| DNA extract | | 5 μL | |
| Final volume | | 20 μL | |

| Program | Temperature | Duration | Number of cycles | Acquisition method |
|---|---|---|---|---|
| UDG | Ambient | 5 min | 1 | None |
| Amplification | | | | |
| Initial denaturation | 95° C. | 10 min | 1 | |
| Denaturation | 95° C. | 10 sec | | None |
| Hybridization | 55° C. | 10 sec | 45 | Single |
| Elongation | 72° C. | 15 sec | | |
| Melting point curve | | | | |
| Denaturation | 95° C. | 0 sec | 1 | None |
| Hybridization | 65° C. | 30 sec | 1 | None |
| Melting | 95° C., 0.1° C./dry | 0 sec | 1 | Continuous |
| Cooling | 40° C. | 30 sec | 1 | |

The results are given in FIG. 1. The simple mutant gyrA83 has a melting point of 56.6° C., the double mutant gyrA83+gyrA87 has a melting point of 50° C., whereas the non-mutated strain Paris has a melting point of 59° C.

Example 2: Evaluation of the Sensitivity and Specificity of the RT-PCR Test on LP-gyrA The sensitivity and the specificity of the RT-PCR test on LP-gyrA were assessed on a large number of strains.

On a collection of strains of *L. pneumophila* sensitive to fluoroquinolones;

| Species | Strain |
|---|---|
| *Legionella pneumophila* | Paris (CIP 107629T) |
| *Legionella pneumophila* | Philadelphia (ATCC 33152) |
| *Legionella pneumophila* | Lens (CIP 108286) |
| *Legionella pneumophila* | Lorraine (CIP 108729) |

On the fluoroquinolone-resistant mutants selected in vitro beforehand and having one or more of the gyrA83 and gyrA87 mutations;

| Species | Strain |
|---|---|
| *Legionella pneumophila* 1 LPPI1 | CIP107629T + gyrA83 (T83I) mutation |
| *Legionella pneumophila* 1 LPPI4 | CIP107629T + gyrA83 (T83I) and gyrA87 (D87N) mutations |
| *Legionella pneumophila* 1 LPPI5 | CIP107629T + gyrA83 (T83I) and gyrA87* (D87H) mutations |

On a collection of strains belonging to different species of *Legionella* other than *L. pneumophila*;

| Species | Strain |
|---|---|
| *Legionella parisiensis* | ATCC 35299 |
| *Legionella parisiensis* | ATCC 700174 |
| *Legionella longbeachae* | ATCC 33462 |
| *Legionella longbeachae* | ATCC 33485 |
| *Legionella bozemanii* | ATCC 33217 |
| *Legionella bozemanii* | ATCC 35545 |
| *Legionella jordanis* | ATCC 700762 |
| *Legionella jordanis* | ATCC 33624 |
| *Legionella tucsonensis* | ATCC 4918 |
| *Legionella gormanii* | ATCC 33297 |
| *Legionella maceachernii* | ATCC 35300 |
| *Legionella anisa* | ATCC 35290 |
| *Legionella lansingensis* | ATCC 49751 |
| *Legionella dumoffi* | ATCC 35280 |
| *Legionella oakridgensis* | ATCC 33761 |
| *Legionella oakridgensis* | ATCC 700515 |
| *Legionella wadsworthii* | ATCC 33877 |
| *Legionella mackelia* | ATCC E1 3525 |
| *Legionella birmingham* | ATCC 700709 |
| *Legionella hackeliae* | ATCC 35999 |
| *Legionella birmingham* | ATCC 73702 |
| *Legionella micdadei* | ATCC 33218 |
| *Legionella donaldsonii* | ATCC LC878 |
| *Legionella feeleii* sg1 | ATCC 35072 |
| *Legionella feeleii* sg2 | ATCC 35849 |
| *Legionella feeleii* | ATCC 700514 |

On a collection of clinical bacterial strains not belonging to the genus *Legionella*, and potentially responsible for infections of the respiratory tract in humans

| Species | Strain |
|---|---|
| *Staphylococcus aureus* | ATCC 12598 |
| *Staphylococcus aureus* | ATCC 29737 |
| *Staphylococcus epidermidis* | ATCC 14990 |
| *Enterococcus faecium* | CIP 54.32 |
| *Corynebacterium jeikeium* | CIP 82.51 |
| *Streptococcus pyogenes* | ATCC 19615 |
| *Streptococcus mitis* | ATCC 49456 |
| *Streptococcus pneumoniae* | ATCC 6303 |
| *Streptococcus pneumoniae* | ATCC 49619 |
| *Bacillus subtilis* | ATCC 6633 |
| *Escherichia coli* | ATCC 25922 |
| *Escherichia coli* | ATCC 35218 |
| *Serratia marcescens* | CIP 103551 |
| *Citrobacter koseri* | ATCC 27156 |
| *Klebsiella pneumoniae* | ATCC 23357 |
| *Pseudomonas aeruginosa* | CIP 5933 |
| *Acinetobacter baumanii* | ATCC 19606 |

Figure 2:
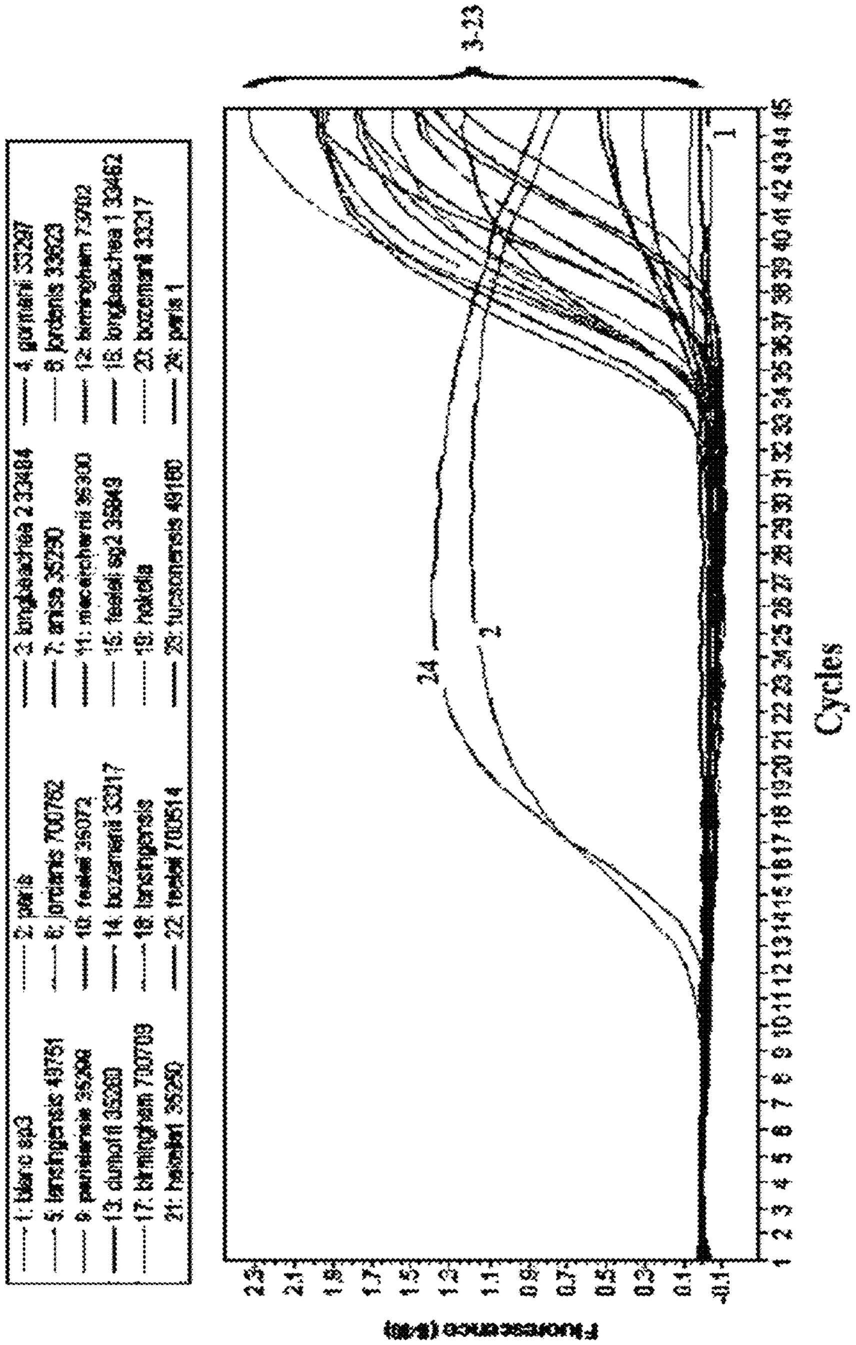
FIG. 2 shows the real-time PCR amplifications of the gyrA gene in different species of *Legionella*. The bacterial inoculum tested for each species is standardized beforehand.
Figure 3:
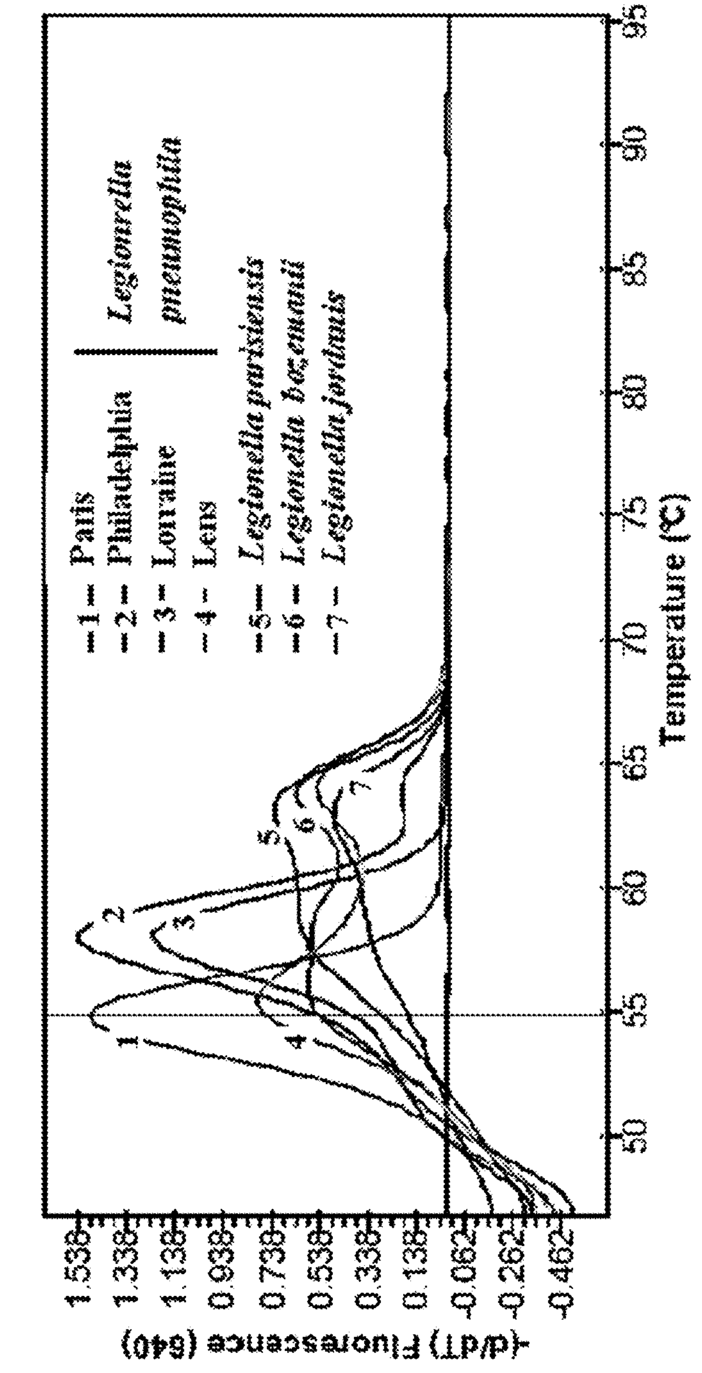
FIG. 3 shows the melting peaks obtained for four strains of *L. pneumophila* and three other species of *Legionella*.

FIG. 2 shows that the test sensitively and specifically detects the target fragment of the gyrA gene of *L. pneumophila*. The primers defined preferentially amplify the gyrA fragment of *L. pneumophila*. However, for a number of amplification cycles greater than or equal to 35, an amplification signal can be observed for other species of this genus. Nevertheless, FIG. 3 shows that the test makes it possible, based on the melting point curves, to distinguish between the strains of *L. pneumophila* (Paris, Philadelphia, Lorraine and Lens strains) and the strains of three other species of *Legionella*. Moreover, the melting points of the strains of *Legionella* not belonging to the species *pneumophila* are higher than those obtained for *L. pneumophila.*

Figure 4:
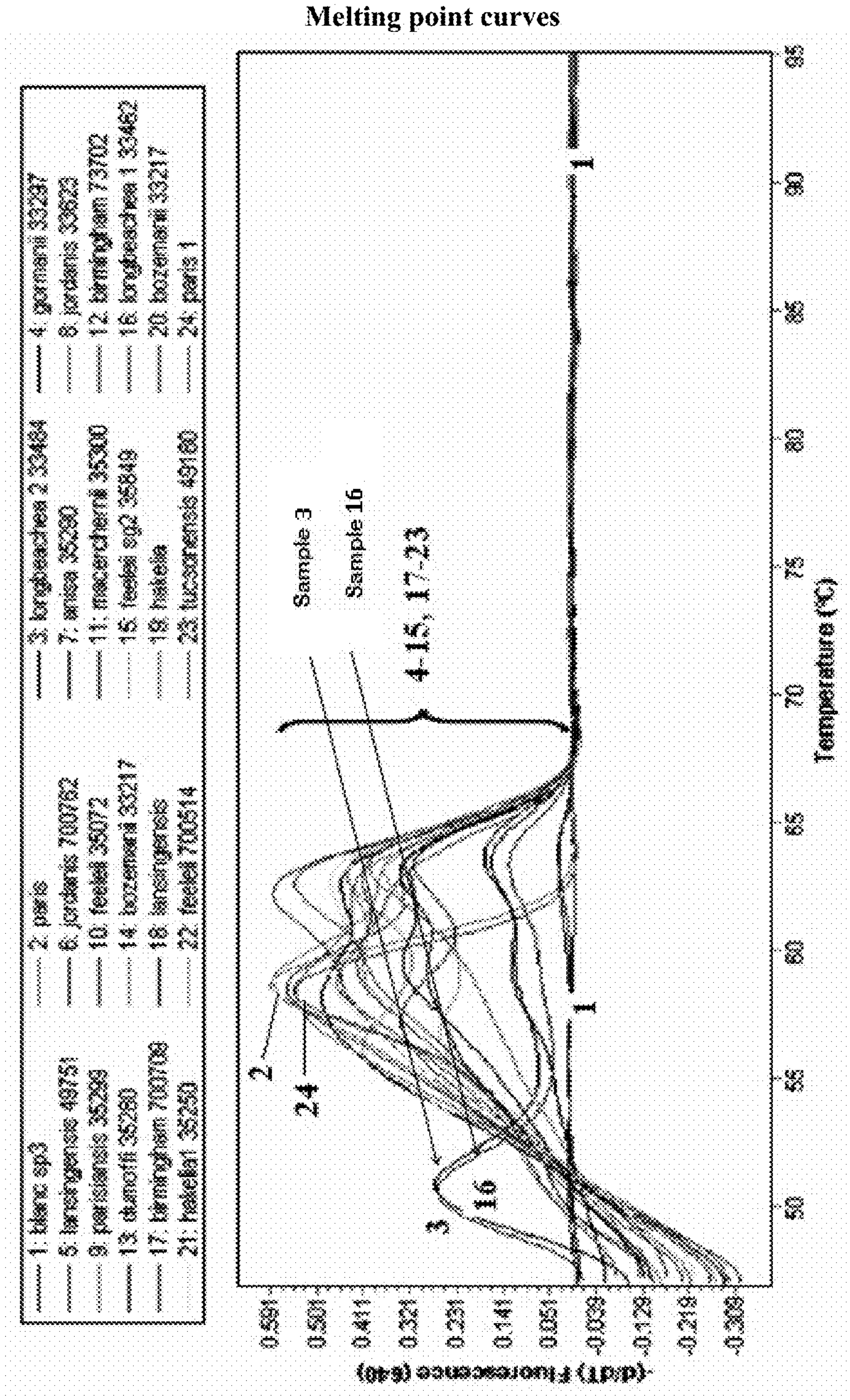
FIG. 4 shows the melting peaks obtained for 2 strains of *L. pneumophila* Paris and 21 strains belonging to other species of *Legionella*.

Similarly, FIG. 4 shows that 21 strains of *Legionella* belonging to species other than *L. pneumophila* have melting points higher than that of *L. pneumophila* strain Paris, with the exception of strains of the species *L. longbeachea* which exhibit a melting peak around 50° C. Nevertheless, they cannot be merged with the melting point curves of the gyrA mutants due to their profile with triple melting peaks (50° C., 60° C., 65° C.).

The analytical sensitivity of the RT-PCR test on LPgyrA was tested on a series of 10-fold dilutions of DNA from *L. pneumophila* Paris, starting with a bacterial inoculum of $8.6 \times 10^7$ bacteria. Table 1 shows the results of this analysis. A suspension containing 9 genome/test copies allows reproducible amplification.

TABLE 1

Amplification of the gyrA gene of *L. pneumophila* Paris starting with a series of 10-fold dilutions of a bacterial inoculum of $8.6 \times 10^7$ bacteria (per test).

| Inc | Pos | Name | Type | CP | Conc | Std |
|---|---|---|---|---|---|---|
| ☒ | 1 | Basic gyrA | Negative control | | | |
| ☒ | 2 | DNA gyrA strain Paris | Standard | 11.27 | 8.60E7 | 9.30E7 |
| ☒ | 3 | DNA gyrA 10-1 | Standard | 15.25 | 1.07E7 | 9.30E6 |
| ☒ | 4 | DNA gyrA 10-2 | Standard | 20.04 | 8.72E5 | 9.30E5 |
| ☒ | 5 | DNA gyrA 10-3 | Standard | 24.08 | 9.53E4 | 9.30E4 |
| ☒ | 6 | DNA gyrA 10-4 | Standard | 27.82 | 1.02E4 | 9.30E3 |
| ☒ | 7 | DNA gyrA 10-5 | Standard | 31.49 | 9.74E2 | 9.30E2 |
| ☒ | 8 | DNA gyrA 10-6 | Standard | 34.87 | 9.67E1 | 9.30E1 |
| ☒ | 9 | DNA gyrA 10-7 | Standard | 38.19 | 8.73E0 | 9.30E0 |
| ☒ | 10 | DNA gyrA 10-8 | Standard | | | 9.30E−1 |
| ☒ | 11 | DNA gyrA 10-9 | Standard | | | 9.30E−2 |

Example 3: Evaluation of the Relevance of the RT-PCR Test on LP-gyrA on Specimens Taken from the Respiratory Tract of Patients Suffering from Legionnaires' Disease Due to *L. pneumophila*

Figure 5:
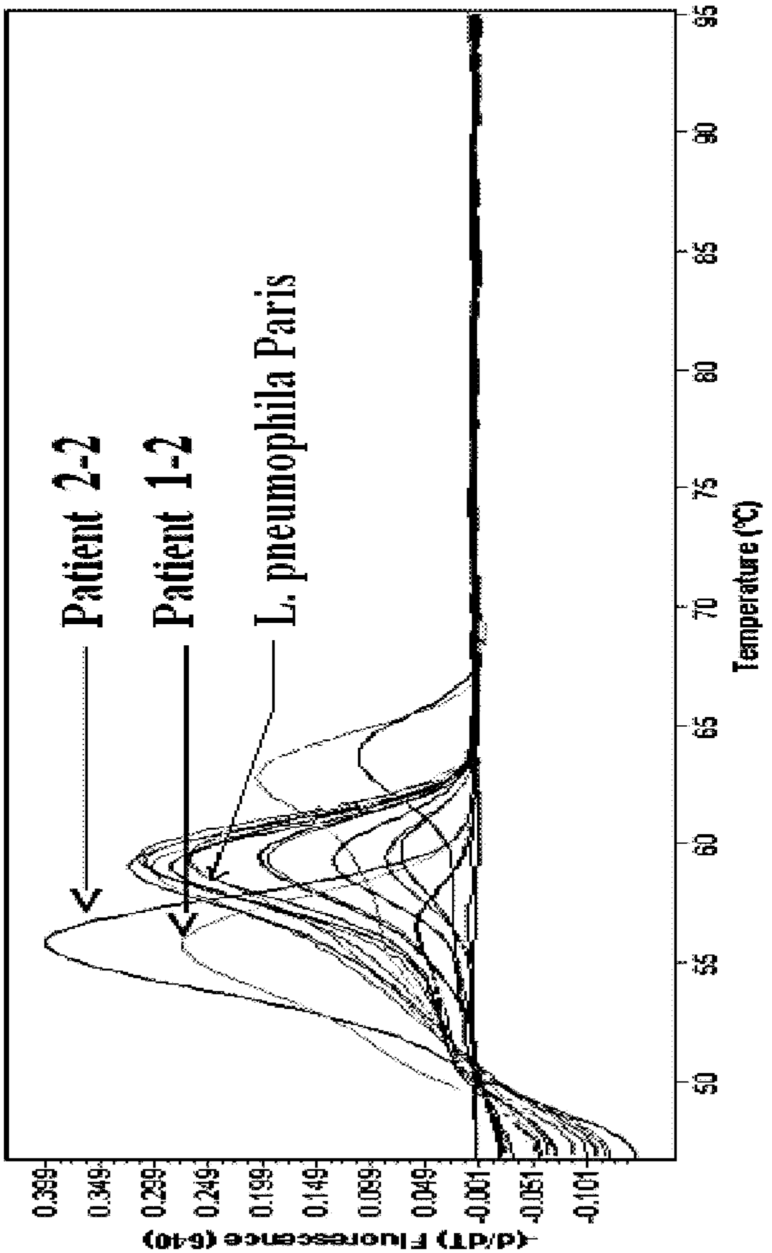
FIG. 5 shows the RT-PCR melting point curves of LP-gyrA showing a melting point (MP) of 59° C. for *L. pneumophila* Paris, and for most respiratory specimens taken from patients suffering from legionnaires' disease. By contrast, specimens 1-2 and 2-2 show a reduction of approximately 4-5° C. in the MP suggesting a mutation of the gyrA gene.

Based on analysis of the expectorations of 82 patients suffering from legionnaires' disease, it was possible to detect the presence of resistant mutated gyrA83 *L. pneumophila*. FIG. 5 shows the melting point curves obtained on the basis of specimens taken from patients suffering from legionnaires' disease. For two patients (1 and 2), the melting point curves (1-2 and 2-2) obtained from clinical specimens collected after establishing antibiotic treatment with a fluoroquinolone, show a melting peak of approximately 55° C. This peak, which is lower that of the control (non-mutated) wild-type *L. pneumophila* Paris suggests the presence of at least one QRDR mutation of gyrA in the strain of *L. pneumophila* infecting each of these patients.

In order to confirm the results obtained for these two patients, the QRDR of the gyrA gene of the infecting strain of *L. pneumophila*, was amplified and sequenced directly from a clinical specimen due to the impossibility of isolating this strain in culture. Two DNA sequencing methods were used: the standard Sanger method and a high-throughput sequencing method making it possible to measure the percentage of mutants with respect to the non-mutated population in the clinical specimen from each of the two patients.

In patient 1, the sequence 1-1 obtained from a clinical specimen collected before treatment with a fluoroquinolone, exhibits no mutation with respect to the strain Paris. After treatment with fluoroquinolone, a mixture of DNA sequences (ACA/ATC, Y=C or T) (sequence 1-2) is noted, which evidences the simultaneous presence of bacteria sensitive to, and bacteria resistant to, fluoroquinolones by a Thr83Ile substitution at position 83 of the GyrA protein.

For patient 2, the DNA sequence before treatment with fluoroquinolone (sequence 2-1) is wild-type (non-mutated). In this patient, it was possible to isolate a strain of *L. pneumophila* in culture from this same clinical specimen. The fact that this strain was very sensitive to the fluoroquinolones was confirmed, phenotypically (antibiogram) and due to the absence of a gyrA mutation after amplification and sequencing of this gene from the strain. By contrast, at different times during the treatment with a fluoroquinolone in this patient 2, the occurrence of a mutated gyrA sequence (ATA instead of ACA) (sequences 2-2, 2-3, 2-4) was demonstrated on three successive specimens leading to the same Thr83Ile substitution responsible for fluoroquinolone resistance in *L. pneumophila.*

Figure 7:
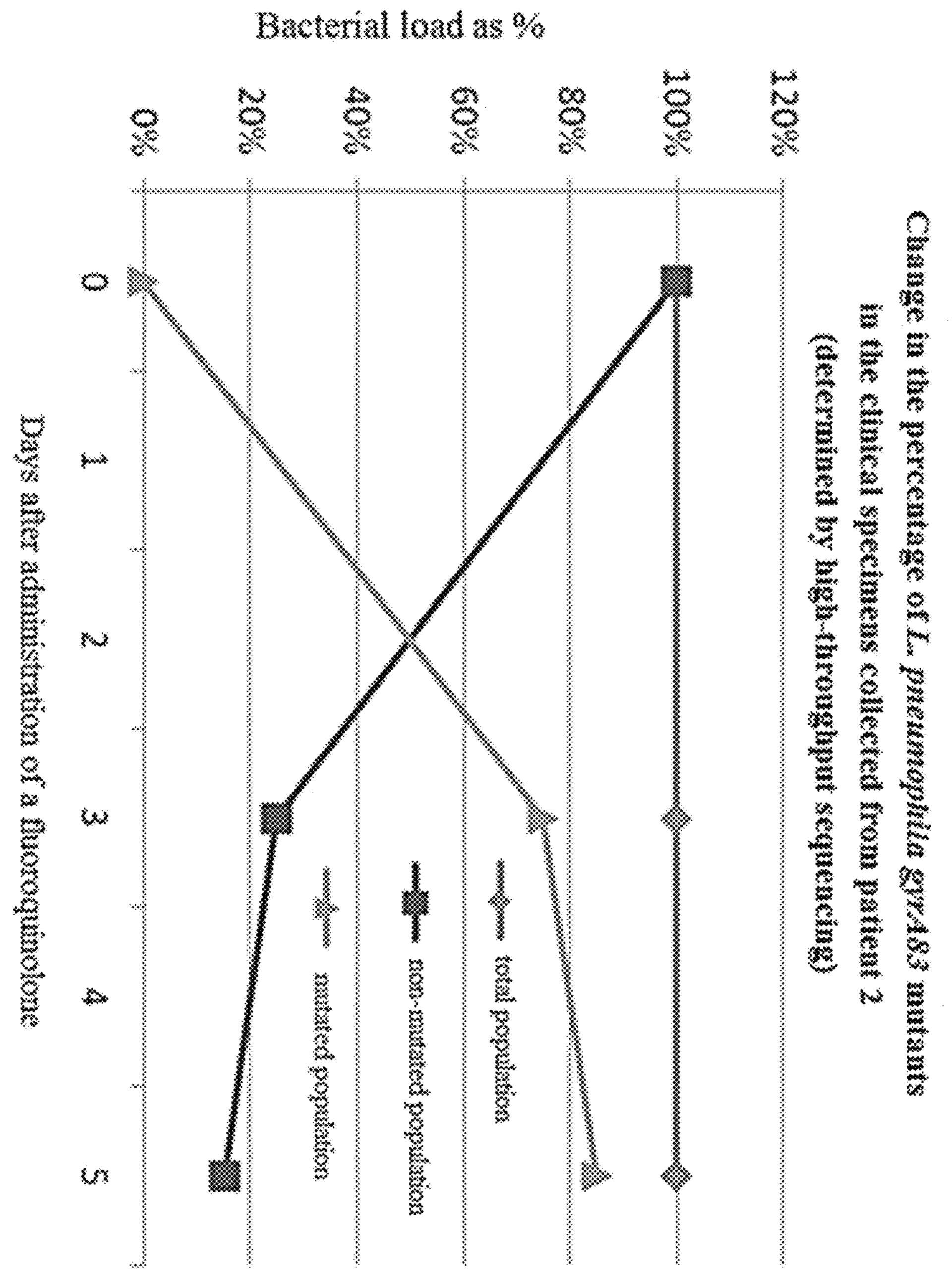
FIG. 7 shows, for patient 2, a progressive increase in the percentage of mutants with respect to the non-mutated population, i.e. a progressive replacement of a population of *L. pneumophila* which is sensitive to the fluoroquinolones by a population which is mostly resistant to these antibiotics.

The high-throughput sequencing data have confirmed the in vivo selection of gyrA83 mutants of *L. pneumophila* in these two patients during treatment with a fluoroquinolone. FIG. 7 shows, for patient 2, a progressive increase in the percentage of mutants with respect to the non-mutated population, i.e. a progressive replacement of a population of *L. pneumophila* which is sensitive to the fluoroquinolones by a population which is mostly resistant to these antibiotics.

All of these data confirm the possibility of selection of fluoroquinolone-resistant strains of *L. pneumophila* in patients infected with this pathogen and treated with one of these antibiotics. They also make it possible to validate the relevance of the RT-PCR test on LP-gyrA, developed in order to detect these resistances on the basis of an isolated strain or directly from clinical specimens.

The invention claimed is:

1. In vitro method of detecting a bacterial strain of *Legionella pneumophila* that is resistant to fluoroquinolone, in a biological sample from a patient suffering from legionnaires' disease, the resistance being acquired in vivo, the method comprising:

detecting:

a mutation on at least one of positions 83 or 87 with respect to SEQ ID NO: 1 in a GyrA protein of *L. pneumophila* having at least 90% identity with SEQ ID NO: 1, said mutation resulting in a mutated GyrA protein, or a nucleic acid encoding said mutated GyrA protein, the detection of said mutation or of the nucleic acid encoding said mutated GyrA protein indicating the presence of fluoroquinolone-resistant bacterial strain *Legionella pneumophila* in the sample.

2. The method according to claim 1, in which the mutated GyrA protein is such that:

the amino acid at position 83 is different from T and the amino acid at position 87 can correspond to any amino acid, or the amino acid at position 87 is different from D, and the amino acid at position 83 can correspond to any amino acid.

3. The method according to claim 1, in which the mutated GyrA protein is such that:

the amino acid at position 83 is: I, L, W, A or V and the amino acid at position 87 can correspond to any amino acid, or the amino acid at position 87 is: N, G, Y, H or V and the amino acid at position 83 can correspond to any amino acid, or the amino acid at position 83 is: I, L, W, A or V, and the amino acid at position 87 is: N, G, Y, H or V.

4. The method according to claim 1, in which said mutated GyrA protein comprises the consensus sequence:

$GDX_1X_2VYX_3T$ (SEQ ID NO: 2), in which:

$X_2$ is A, $X_1$ and $X_3$ correspond to the mutations at positions 83 and 87 respectively, and $X_1$ is different from T, and $X_3$ is any amino acid, or $X_3$ is different from D, and $X_1$ any amino acid.

5. The method according to claim 4, in which:

$X_1$ is I, L, W, A or V, and $X_3$ corresponds to any amino acid, or $X_3$ is N, G, Y, H or V, and $X_1$ corresponds to any amino acid, or $X_1$ is I, L, W, A or V, and $X_3$ is N, G, Y, H or V.

6. The method according to claim 1, wherein the nucleic acid encoding said mutated GyrA protein has at least one nucleotide substitution with respect to SEQ ID NO: 3, at a position equivalent to position 7, 8, 19, 20 or 21 with respect to SEQ ID NO: 3, and wherein nucleotides at positions 7 and 8 correspond to two nucleotides of a codon encoding an amino acid at position 83 of the GyrA protein, and nucleotides at positions 19, 20 and 21 correspond to three nucleotides of a codon encoding an amino acid at position 87 of the GyrA protein.

7. The method according to claim 1, wherein the detection of said mutated GyrA protein or of the nucleic acid encoding said mutated GyrA protein is carried out by a technique selected from the group consisting of: western blot, northern blot, southern blot, PCR, real-time PCR, PCR hybridization, PCR array, TMA, NASBA, LCR, DNA/RNA hybridization, DNA chip, DNA/RNA sequencing, dot-blot, and RFLP (Restriction fragment length polymorphism).

8. The method according to claim 1, said method comprising the steps of:

a) bringing a biological sample likely to contain a target nucleic acid belonging to a fluoroquinolone-resistant bacterial strain of *Legionella pneumophila*, into contact with a pair of primers capable of hybridizing specifically with said target nucleic acid, b) PCR amplification of said target nucleic acid using the pair of primers in order to obtain an amplification product, said amplification product comprising nucleic acid comprising a sequence having at least 90% identity with sequence SEQ ID NO: 3, and c) detecting a nucleic acid encoding the mutated GyrA protein, wherein the detection of the nucleic acid encoding said mutated GyrA protein indicates the presence of a fluoroquinolone-resistant bacterial strain of *Legionella pneumophila*, in the sample.

9. The method according to claim 8, wherein the detection of said amplification product is carried out using at least one nucleotide probe capable of hybridizing with the amplification product.

10. The method according to claim 1, wherein the detection of the nucleic acid encoding said mutated GyrA protein is carried out using at least one nucleotide probe, said at least one nucleotide probe comprising a nucleic acid molecule having at least 90% identity with sequence SEQ ID NO: 3, said at least one nucleotide probe being linked by a covalent bond to at least one marker molecule allowing detection thereof, said marker molecule being a fluorochrome or a radioactive isotope.

11. The method according to claim 1, wherein the detection of the nucleic acid encoding said mutated GyrA protein is carried out using at least one nucleotide, said at least one nucleotide probe comprising a nucleic acid molecule having at least 90% identity with sequence SEQ ID NO: 60 linked by a covalent bond to a fluorochrome.

12. The method according to claim 1, further comprising carrying out PCR amplification a fragment of the gyrA gene of *Legionella pneumophila* with a pair of primers comprising a primer having at least 90% identity with sequence SEQ ID NO: 58, and a primer having at least 90% identity with sequence SEQ ID NO: 59, and wherein the nucleic acid encoding said mutated GyrA protein is detected.

13. The method according to claim 12, wherein the detection the nucleic acid encoding said mutated GyrA protein is carried out using at least one nucleotide probe comprising a nucleic acid molecule having at least 90% identity with sequence SEQ ID NO: 60 linked by a covalent bond to a fluorochrome.

14. A method for determining an infection with a *Legionella pneumophila* bacterium that is resistant to fluoroquinolone in a patient, or for determining or predicting the efficacy of a treatment with fluoroquinolones in a patient infected with the *Legionella pneumophila* bacterium, the method comprising performing the method of claim 1.

15. The method according to claim 2, in which the mutated GyrA protein is such that:

the amino acid at position 83 is: I, L, W, A or V and the amino acid at position 87 can correspond to any amino acid, or the amino acid at position 87 is: N, G, Y, H or V and the amino acid at position 83 can correspond to any amino acid, or the amino acid at position 83 is: I, L, W, A or V, and the amino acid at position 87 is: N, G, Y, H or V.

16. The method according to claim 2, wherein the nucleic acid encoding said mutated GyrA protein has at least one nucleotide substitution with respect to SEQ ID NO: 3, at a position equivalent to position 7, 8, 19, 20 or 21 with respect to SEQ ID NO: 3, and wherein the nucleotides at positions 7 and 8 correspond to two nucleotides of a codon encoding the amino acid at position 83 of the GyrA protein, and the nucleotides at positions 19, 20 and 21 correspond to three nucleotides of a codon encoding the amino acid at position 87 of the GyrA protein.

17. The method according to claim 3, wherein the nucleic acid encoding said mutated GyrA protein has at least one nucleotide substitution with respect to SEQ ID NO: 3, at a position equivalent to position 7, 8, 19, 20 or 21 with respect to SEQ ID NO: 3, and wherein the nucleotides at positions 7 and 8 correspond to two nucleotides of a codon encoding the amino acid at position 83 of the GyrA protein, and the nucleotides at positions 19, 20 and 21 correspond to three nucleotides of a codon encoding the amino acid at position 87 of the GyrA protein.

18. The method according to claim 4, wherein the nucleic acid encoding said mutated GyrA protein has at least one nucleotide substitution with respect to SEQ ID NO: 3, at a position equivalent to position 7, 8, 19, 20 or 21 with respect to SEQ ID NO: 3, and wherein the nucleotides at positions 7 and 8 correspond to two nucleotides of a codon encoding the amino acid at position 83 of the GyrA protein, and the nucleotides at positions 19, 20 and 21 correspond to three nucleotides of a codon encoding the amino acid at position 87 of the GyrA protein.

19. The method according to claim 5, wherein the nucleic acid encoding said mutated GyrA protein has at least one nucleotide substitution with respect to SEQ ID NO:

3, at a position equivalent to position 7, 8, 19, 20 or 21 with respect to SEQ ID NO: 3, and wherein the nucleotides at positions 7 and 8 correspond to two nucleotides of a codon encoding the amino acid at position 83 of the GyrA protein, and the nucleotides at positions 19, 20 and 21 correspond to three nucleotides of a codon encoding the amino acid at position 87 of the GyrA protein.

20. The method according to claim 2, the detection of the presence of said mutated GyrA protein or of the target nucleic acid encoding said mutated GyrA protein being carried out by a technique chosen from: western blot, northern blot, southern blot, PCR, real-time PCR, PCR hybridization, PCR array, TMA, NASBA, LCR, DNA/RNA hybridization, DNA chip, DNA/RNA sequencing, dot-blot, the RFLP (Restriction fragment length polymorphism) technique.

21. An in vitro method of detecting a bacterial strain of *Legionella pneumophila* that is resistant to fluoroquinolone, in a biological sample from a patient suffering from legionnaires' disease, the resistance being acquired in vivo, and treating said patient by a modified treatment schedule, the method comprising:

providing the biological sample;

conducting real time PCR in the presence of a pair of probes, the probes comprising an anchoring probe having at least 90% identity with the sequence of SEQ ID NO: 60, the anchoring probe covalently bonded to a first fluorescent marker molecule, and a detection probe having at least 90% identity with the sequence of SEQ ID NO: 3, the detection probe covalently bonded to a second fluorescent marker molecule, wherein the anchoring probe and the detection probe hybridize to a target nucleic acid molecule within a distance of less than ten nucleotides, and the first and second fluorescent marker molecules interact to cause Fluorescent Resonance Energy Transfer (FRET);

detecting the presence of a mutation at position 83 and/or position 87 with respect to SEQ ID NO: 1 in a GyrA protein of *L. pneumophila*, said mutation indicating the presence of a bacterial strain of *Legionella pneumophila* that is resistant to fluoroquinolone in the sample; and treating a patient in which said mutation is detected using a treatment based on said detecting.

22. An in vitro method of detecting a bacterial strain of *Legionella pneumophila* that is resistant to fluoroquinolone, in a biological sample from a patient suffering from legionnaires' disease, the resistance being acquired in vivo, and treating said patient by a treatment based on said detecting, the method comprising:

performing the method of claim 1 in which either said mutation in said GyrA protein or the nucleic acid encoding said mutated GyrA protein is detected; and treating a patient in which said mutation or the nucleic acid encoding said mutated GyrA protein is detected using a treatment based on said detecting.

* * * * *

SEQUENCE LISTING

```
<160> NUMBER OF SEQ ID NOS: 62

<210> SEQ ID NO 1
<211> LENGTH: 863
<212> TYPE: PRT
<213> ORGANISM: Legionella pneumophila

<400> SEQUENCE: 1

Met Val Tyr Leu Ala Lys Glu Val Leu Pro Val Asn Ile Glu Asp Glu
1               5                   10                  15

Leu Lys Gln Ser Tyr Leu Asp Tyr Ala Met Ser Val Ile Val Gly Arg
            20                  25                  30

Ala Leu Pro Asp Val Arg Asp Gly Leu Lys Pro Val His Arg Arg Val
        35                  40                  45

Leu Phe Ala Met Ser Glu Leu Gly Asn Asp Trp Asn Lys Pro Tyr Lys
    50                  55                  60

Lys Ser Ala Arg Val Val Gly Asp Val Ile Gly Lys Tyr His Pro His
65                  70                  75                  80

Gly Asp Thr Ala Val Tyr Asp Thr Ile Val Arg Met Ala Gln Pro Phe
                85                  90                  95

Ser Met Arg Tyr Leu Leu Ile Asp Gly Gln Gly Asn Phe Gly Ser Val
            100                 105                 110

Asp Gly Asp Ala Pro Ala Ala Met Arg Tyr Thr Glu Val Arg Met Ser
        115                 120                 125

Lys Val Ala His Ala Leu Leu Ala Asp Leu Asp Lys Glu Thr Val Asp
    130                 135                 140

Phe Ser Pro Asn Tyr Asp Glu Thr Glu Phe Ala Pro Val Val Leu Pro
145                 150                 155                 160

Ser Arg Ile Pro Asn Leu Leu Val Asn Gly Ser Ser Gly Ile Ala Val
                165                 170                 175

Gly Met Ala Thr Asn Ile Pro Pro His Asn Leu Thr Glu Val Ile Asn
            180                 185                 190

Ala Cys Ile Ala Leu Val Asp Glu Pro Asp Thr Ser Leu Glu Asp Leu
        195                 200                 205

Met Glu Ile Ile Pro Gly Pro Asp Phe Pro Thr Ala Ala Ile Ile Asn
    210                 215                 220

Gly Arg Ala Gly Ile Ile Glu Gly Tyr Arg Thr Gly Lys Gly Arg Val
225                 230                 235                 240

Val Ile Arg Ala Arg Thr Glu Ile Glu Thr Asp Glu Ser Ser Gly Arg
                245                 250                 255

Gln Ser Ile Ile Ile Gln Glu Leu Pro Tyr Gln Val Asn Lys Ala Arg
            260                 265                 270

Leu Ile Glu Arg Ile Ala Glu Leu Val Arg Asp Lys Lys Val Glu Gly
        275                 280                 285

Ile Ser Gly Leu Arg Asp Glu Ser Asp Lys Gln Gly Met Arg Val Val
    290                 295                 300

Ile Glu Leu Lys Arg Asn Glu Val Ala Asp Val Val Leu Asn Asn Leu
305                 310                 315                 320

Phe Ala His Thr Gln Met Gln Asn Val Phe Gly Ile Asn Met Val Ala
                325                 330                 335

Leu Val Asp Gly Gln Pro Arg Thr Leu Asn Leu Lys Gln Ile Leu Glu
            340                 345                 350

Tyr Phe Ile Lys His Arg Arg Glu Val Val Thr Arg Arg Thr Ile Phe
        355                 360                 365
```

```
Glu Leu Lys Lys Ala Arg Ser Arg Ala His Leu Leu Glu Gly Leu Gly
    370                 375                 380

Ile Ala Leu Ala Asn Ile Asp Glu Met Ile Ala Leu Ile Lys Gln Ser
385                 390                 395                 400

Pro Thr Pro Gln Asp Ala Lys Ser Ala Leu Leu Ser Lys Ile Trp Gln
                405                 410                 415

Pro Gly Leu Val Lys Ala Met Leu Glu Lys Ala Gly Ser Asn Ala Ser
            420                 425                 430

Arg Pro Asp Asp Leu Thr Glu Glu Tyr Gly Leu His Glu Asn Gly Tyr
        435                 440                 445

Lys Leu Ser Glu Ala Gln Ala Gln Ala Ile Leu Glu Leu Arg Leu His
    450                 455                 460

Arg Leu Thr Ala Leu Glu Gln Asp Lys Ile Ile Asn Glu Phe Glu Glu
465                 470                 475                 480

Leu Leu Asn Leu Ile Lys Glu Leu Leu Asp Ile Leu Ala Ser Pro Glu
                485                 490                 495

Arg Leu Met Gln Val Ile Arg Asp Glu Leu Ile Glu Ile Lys Ser Gln
            500                 505                 510

Phe Gly Asp Glu Arg Arg Thr Glu Ile Thr Ala Ser Gln Glu Asp Leu
        515                 520                 525

Thr Ile Glu Asp Leu Ile Thr Glu Glu Asp Val Val Val Thr Leu Ser
    530                 535                 540

His Gln Gly Tyr Val Lys Tyr Gln Pro Ile Thr Ala Tyr Gln Ala Gln
545                 550                 555                 560

Arg Arg Gly Gly Lys Gly Lys Ser Ala Thr His Val Lys Asp Glu Asp
                565                 570                 575

Phe Val Glu Arg Leu Val Ile Ala Ser Thr His Asp Thr Leu Leu Cys
            580                 585                 590

Phe Ser Asn His Gly Lys Leu Tyr Trp Leu Lys Ala Tyr Gln Leu Pro
        595                 600                 605

Gln Ala Ser Arg Ala Ser Arg Gly Arg Pro Ile Ile Asn Ile Leu Pro
    610                 615                 620

Leu Ala Glu Gly Glu Glu Ile Asn Ala Met Leu Pro Val Arg Glu Tyr
625                 630                 635                 640

Lys Asp Gly Ser Tyr Val Phe Met Ala Thr Lys Lys Gly Thr Val Lys
                645                 650                 655

Lys Val Pro Leu Asn Ala Phe Ser Arg Pro Arg Ser Asn Gly Ile Ile
            660                 665                 670

Ala Val Asp Leu Glu Glu Asp Asp Ser Leu Val Gly Val Asp Ile Thr
        675                 680                 685

Asp Gly Thr Arg Asp Ile Met Leu Phe Thr Asp Ala Gly Lys Val Ile
    690                 695                 700

Arg Phe Asp Glu Asn Lys Val Arg Pro Met Gly Arg Thr Ala Arg Gly
705                 710                 715                 720

Val Arg Gly Ile Arg Val Glu Lys Asp Gln Ala Val Lys Ser Leu Val
                725                 730                 735

Val Val Asp Pro Asn Gly Gly Thr Ile Leu Thr Ala Thr Glu Asn Gly
            740                 745                 750

Tyr Gly Lys Arg Thr His Ile Asp Glu Tyr Arg Val Ser Gly Arg Gly
        755                 760                 765

Gly Gln Gly Val Ile Ser Ile Gln Val Thr Glu Arg Asn Gly Lys Val
    770                 775                 780

Val Arg Ser Leu Gln Val Thr Asp Asn Asp Glu Ala Met Leu Ile Thr
```

-continued

```
785                 790                 795                 800

Asp Lys Gly Thr Leu Val Arg Phe Lys Val Asn Glu Leu Ser Val Ile
                805                 810                 815

Gly Arg Asn Thr Gln Gly Val Arg Leu Ile Asn Val Ser Ser Gly Glu
            820                 825                 830

Thr Val Val Gly Met Gln Lys Ile Val Asp Leu Gly Glu Glu Leu Glu
        835                 840                 845

Glu Ala Glu Asp Ser Ser Leu Asn Ala Glu Asp Asn Ser Asp Glu
    850                 855                 860


<210> SEQ ID NO 2
<211> LENGTH: 8
<212> TYPE: PRT
<213> ORGANISM: Unknown
<220> FEATURE:
<223> OTHER INFORMATION: Artificial Sequence
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 2

Gly Asp Xaa Xaa Val Tyr Xaa Thr
1               5


<210> SEQ ID NO 3
<211> LENGTH: 23
<212> TYPE: DNA
<213> ORGANISM: Legionella pneumophila

<400> SEQUENCE: 3

ggggatacag ctgtttatga cac                                              23


<210> SEQ ID NO 4
<211> LENGTH: 23
<212> TYPE: DNA
<213> ORGANISM: Legionella pneumophila

<400> SEQUENCE: 4

ggggattcag ctgtttatga cac                                              23


<210> SEQ ID NO 5
<211> LENGTH: 23
<212> TYPE: DNA
<213> ORGANISM: Legionella pneumophila

<400> SEQUENCE: 5

ggggatccag ctgtttatga cac                                              23


<210> SEQ ID NO 6
<211> LENGTH: 23
<212> TYPE: DNA
<213> ORGANISM: Legionella pneumophila

<400> SEQUENCE: 6

ggggatgcag ctgtttatga cac                                              23


<210> SEQ ID NO 7
<211> LENGTH: 23
<212> TYPE: DNA
```

<213> ORGANISM: Legionella pneumophila

<400> SEQUENCE: 7
ggggataaag ctgtttatga cac 23

<210> SEQ ID NO 8
<211> LENGTH: 23
<212> TYPE: DNA
<213> ORGANISM: Legionella pneumophila

<400> SEQUENCE: 8
ggggatatag ctgtttatga cac 23

<210> SEQ ID NO 9
<211> LENGTH: 23
<212> TYPE: DNA
<213> ORGANISM: Legionella pneumophila

<400> SEQUENCE: 9
ggggatagag ctgtttatga cac 23

<210> SEQ ID NO 10
<211> LENGTH: 23
<212> TYPE: DNA
<213> ORGANISM: Legionella pneumophila

<400> SEQUENCE: 10
ggggatacaa ctgtttatga cac 23

<210> SEQ ID NO 11
<211> LENGTH: 23
<212> TYPE: DNA
<213> ORGANISM: Legionella pneumophila

<400> SEQUENCE: 11
ggggatacat ctgtttatga cac 23

<210> SEQ ID NO 12
<211> LENGTH: 23
<212> TYPE: DNA
<213> ORGANISM: Legionella pneumophila

<400> SEQUENCE: 12
ggggatacac ctgtttatga cac 23

<210> SEQ ID NO 13
<211> LENGTH: 2592
<212> TYPE: DNA
<213> ORGANISM: Legionella pneumophila

<400> SEQUENCE: 13
atggtatacc tagccaaaga agtcttacca gtcaacatag aagacgaatt gaagcaatcc 60
tatttggatt atgcgatgag tgtcattgta ggccgagcgt tgcctgatgt acgtgatggt 120
ttaaaaccgg tgcataggcg agttcttttt gcgatgagcg agttgggtaa tgattggaat 180
aaaccttata aaaaatctgc tcgtgtagta ggggatgtca tcggtaaata ccatcctcac 240
ggggatacag ctgtttatga caccattgtt cgtatggccc aaccttttc catgcgctac 300 cttttaatcg atggacaggg gaattttggc tctgtagatg gagatgctcc agctgccatg 360
cgttacactg aagtaagaat gtccaaagtg gcgcatgctt tactggctga tttggataag 420
gaaactgttg attttagccc taactatgat gaaacagaat ttgctccagt ggtattgcca 480

-continued

```
tcgagaattc ccaatttact agttaatggc tcttccggta ttgcggtagg gatggctact    540
aatattccac cacataatct taccgaagta atcaatgcat gtattgcctt agtggatgaa    600
cctgacacga gtcttgaaga tttaatggaa attattcctg gccctgattt tcctacagca    660
gcaattatta atggtcgtgc tggaattatt gaaggttatc gtactggaaa agggcgggtt    720
gttatcaggg cacgaacaga aattgaaacg gatgaaagtt caggccgtca gtcaattatt    780
attcaggaat taccctatca ggtgaataaa gcgcgtttga tcgagcgtat tgctgaattg    840
gtaagggata agaaagtcga gggaatttcc ggcttgaggg atgagtcaga caagcaggga    900
atgagagtag tcattgaatt aaaacgcaat gaagtagcag atgtggtatt gaataacctg    960
ttcgctcata ctcaaatgca aaatgtattc ggaattaata tggttgcttt ggtggatggc   1020
caaccgcgta ctttgaattt gaagcaaata ctggaatatt ttataaaaca tcgaagagag   1080
gttgttacca gacgcacaat atttgaattg aaaaaagcca gaagtcgagc tcatttattg   1140
gagggcttgg gaatcgcctt agctaatatc gatgaaatga tcgcattaat taagcaatct   1200
cctactcctc aagacgcaaa aagtgcttta ttaagcaaaa tatggcaacc tggcttagta   1260
aaggccatgt tggaaaaggc tggctcaaac gcgtcaaggc ctgatgattt aactgaagag   1320
tatggtttgc atgagaacgg atataaatta tctgaagcgc aggcacaagc aatacttgaa   1380
ttaagattac ataggctaac agctcttgaa caagataaaa taattaatga atttgaagag   1440
ctattgaatt taattaaaga attgcttgac atattggctt cacctgaaag acttatgcaa   1500
gttattcgtg atgaattgat agagattaaa tcccaatttg gtgatgagag gcgaacggaa   1560
ataacagcct cacaagaaga tttgactatt gaagatttga ttaccgaaga agacgttgtg   1620
gtcactttat ctcatcaagg ttatgtaaaa tatcagccca ttacagccta tcaggctcag   1680
cgccgaggtg gcaaaggcaa atcggcaact catgtcaagg atgaggattt tgttgagcgt   1740
ttagtgattg ctagtactca tgatacctta ttgtgtttct ccaatcatgg caaattatat   1800
tggctaaaag catatcaatt gcctcaagca agccgcgctt cgagaggaag gcctataatc   1860
aatattcttc ctttggcaga aggcgaagag attaatgcta tgctccctgt ccgtgagtat   1920
aaagacggca gctatgtgtt tatggcaacc aagaagggaa cagttaaaaa agtgccttta   1980
aacgcattta gcaggccgcg ttccaatggt attattgctg tggacctgga agaagatgac   2040
agcctcgtcg gagtcgatat tactgatggt actcgcgata ttatgttgtt tactgatgca   2100
ggcaaagtaa tccgttttga tgaaaataaa gtgcgaccta tggggcgcac ggctcgaggg   2160
gttcgcggaa ttcgagtaga aaaggatcaa gccgttaaat ctcttgtggt agtcgaccca   2220
aatggaggca ccattttgac tgcaactgaa aacggctacg gtaagagaac ccatatcgat   2280
gagtatcgag tgtcaggacg gggaggacaa ggtgttattt ccattcaggt tactgaacga   2340
aatggtaaag tggtccgttc cttgcaggtt accgataatg acgaagccat gttaattaca   2400
gataaaggaa ctttggttcg ttttaaagtc aatgaattat ctgtgatagg cagaaataca   2460
caaggggttc gcctgattaa tgtcagttct ggtgagacag ttgttggaat gcaaaaaatt   2520
gtagatcttg gagaagaatt agaagaagca gaagattcat ctcttaatgc cgaagacaac   2580
agtgatgaat ag                                                       2592
```

<210> SEQ ID NO 14
<211> LENGTH: 23
<212> TYPE: DNA
<213> ORGANISM: Legionella pneumophila

<400> SEQUENCE: 14
ggggatacag atgtttatga cac 23

<210> SEQ ID NO 15
<211> LENGTH: 23
<212> TYPE: DNA
<213> ORGANISM: Legionella pneumophila

<400> SEQUENCE: 15
ggggatacag ttgtttatga cac 23

<210> SEQ ID NO 16
<211> LENGTH: 23
<212> TYPE: DNA
<213> ORGANISM: Legionella pneumophila

<400> SEQUENCE: 16
ggggatacag gtgtttatga cac 23

<210> SEQ ID NO 17
<211> LENGTH: 23
<212> TYPE: DNA
<213> ORGANISM: Legionella pneumophila

<400> SEQUENCE: 17
ggggatacag ctgtttataa cac 23

<210> SEQ ID NO 18
<211> LENGTH: 23
<212> TYPE: DNA
<213> ORGANISM: Legionella pneumophila

<400> SEQUENCE: 18
ggggatacag ctgtttatta cac 23

<210> SEQ ID NO 19
<211> LENGTH: 23
<212> TYPE: DNA
<213> ORGANISM: Legionella pneumophila

<400> SEQUENCE: 19
ggggatacag ctgtttatca cac 23

<210> SEQ ID NO 20
<211> LENGTH: 23
<212> TYPE: DNA
<213> ORGANISM: Legionella pneumophila

<400> SEQUENCE: 20
ggggatacag ctgtttatgt cac 23

<210> SEQ ID NO 21
<211> LENGTH: 23
<212> TYPE: DNA
<213> ORGANISM: Legionella pneumophila

<400> SEQUENCE: 21
ggggatacag ctgtttatgg cac 23

<210> SEQ ID NO 22
<211> LENGTH: 23
<212> TYPE: DNA
<213> ORGANISM: Legionella pneumophila

<400> SEQUENCE: 22
ggggatacag ctgtttatgc cac 23

<210> SEQ ID NO 23
<211> LENGTH: 23
<212> TYPE: DNA
<213> ORGANISM: Legionella pneumophila

<400> SEQUENCE: 23
ggggatacag ctgtttatga gac 23

<210> SEQ ID NO 24
<211> LENGTH: 23
<212> TYPE: DNA
<213> ORGANISM: Legionella pneumophila

<400> SEQUENCE: 24
ggggatacag ctgtttatga aac 23

<210> SEQ ID NO 25
<211> LENGTH: 23
<212> TYPE: DNA
<213> ORGANISM: Legionella pneumophila

<400> SEQUENCE: 25
ggggatttag ctgtttatga cac 23

<210> SEQ ID NO 26
<211> LENGTH: 23
<212> TYPE: DNA
<213> ORGANISM: Legionella pneumophila

<400> SEQUENCE: 26
ggggatttgg ctgtttatga cac 23

<210> SEQ ID NO 27
<211> LENGTH: 23
<212> TYPE: DNA
<213> ORGANISM: Legionella pneumophila

<400> SEQUENCE: 27
ggggatcttg ctgtttatga cac 23

<210> SEQ ID NO 28
<211> LENGTH: 23
<212> TYPE: DNA
<213> ORGANISM: Legionella pneumophila

<400> SEQUENCE: 28
ggggatctcg ctgtttatga cac 23

<210> SEQ ID NO 29
<211> LENGTH: 23
<212> TYPE: DNA
<213> ORGANISM: Legionella pneumophila

<400> SEQUENCE: 29
ggggatctag ctgtttatga cac 23

<210> SEQ ID NO 30
<211> LENGTH: 23
<212> TYPE: DNA

<213> ORGANISM: Legionella pneumophila

<400> SEQUENCE: 30
ggggatctgg ctgtttatga cac 23

<210> SEQ ID NO 31
<211> LENGTH: 23
<212> TYPE: DNA
<213> ORGANISM: Legionella pneumophila

<400> SEQUENCE: 31
ggggattggg ctgtttatga cac 23

<210> SEQ ID NO 32
<211> LENGTH: 23
<212> TYPE: DNA
<213> ORGANISM: Legionella pneumophila

<400> SEQUENCE: 32
ggggatgctg ctgtttatga cac 23

<210> SEQ ID NO 33
<211> LENGTH: 23
<212> TYPE: DNA
<213> ORGANISM: Legionella pneumophila

<400> SEQUENCE: 33
ggggatgccg ctgtttatga cac 23

<210> SEQ ID NO 34
<211> LENGTH: 23
<212> TYPE: DNA
<213> ORGANISM: Legionella pneumophila

<400> SEQUENCE: 34
ggggatgcgg ctgtttatga cac 23

<210> SEQ ID NO 35
<211> LENGTH: 23
<212> TYPE: DNA
<213> ORGANISM: Legionella pneumophila

<400> SEQUENCE: 35
ggggatgttg ctgtttatga cac 23

<210> SEQ ID NO 36
<211> LENGTH: 23
<212> TYPE: DNA
<213> ORGANISM: Legionella pneumophila

<400> SEQUENCE: 36
ggggatgtcg ctgtttatga cac 23

<210> SEQ ID NO 37
<211> LENGTH: 23
<212> TYPE: DNA
<213> ORGANISM: Legionella pneumophila

<400> SEQUENCE: 37
ggggatgtag ctgtttatga cac 23

<210> SEQ ID NO 38
<211> LENGTH: 23

-continued

<212> TYPE: DNA
<213> ORGANISM: Legionella pneumophila

<400> SEQUENCE: 38
ggggatgtgg ctgtttatga cac 23

<210> SEQ ID NO 39
<211> LENGTH: 23
<212> TYPE: DNA
<213> ORGANISM: Legionella pneumophila

<400> SEQUENCE: 39
ggggatacac ccgtttatga cac 23

<210> SEQ ID NO 40
<211> LENGTH: 23
<212> TYPE: DNA
<213> ORGANISM: Legionella pneumophila

<400> SEQUENCE: 40
ggggatacac cagtttatga cac 23

<210> SEQ ID NO 41
<211> LENGTH: 23
<212> TYPE: DNA
<213> ORGANISM: Legionella pneumophila

<400> SEQUENCE: 41
ggggatacac cggtttatga cac 23

<210> SEQ ID NO 42
<211> LENGTH: 23
<212> TYPE: DNA
<213> ORGANISM: Legionella pneumophila

<400> SEQUENCE: 42
ggggatacag tcgtttatga cac 23

<210> SEQ ID NO 43
<211> LENGTH: 23
<212> TYPE: DNA
<213> ORGANISM: Legionella pneumophila

<400> SEQUENCE: 43
ggggatacag tagtttatga cac 23

<210> SEQ ID NO 44
<211> LENGTH: 23
<212> TYPE: DNA
<213> ORGANISM: Legionella pneumophila

<400> SEQUENCE: 44
ggggatacag tggtttatga cac 23

<210> SEQ ID NO 45
<211> LENGTH: 23
<212> TYPE: DNA
<213> ORGANISM: Legionella pneumophila

<400> SEQUENCE: 45
ggggatacag ctgtttataa tac 23

<210> SEQ ID NO 46

<211> LENGTH: 23
<212> TYPE: DNA
<213> ORGANISM: Legionella pneumophila

<400> SEQUENCE: 46
ggggatacag ctgtttatgg tac 23

<210> SEQ ID NO 47
<211> LENGTH: 23
<212> TYPE: DNA
<213> ORGANISM: Legionella pneumophila

<400> SEQUENCE: 47
ggggatacag ctgtttatgg aac 23

<210> SEQ ID NO 48
<211> LENGTH: 23
<212> TYPE: DNA
<213> ORGANISM: Legionella pneumophila

<400> SEQUENCE: 48
ggggatacag ctgtttatgg gac 23

<210> SEQ ID NO 49
<211> LENGTH: 23
<212> TYPE: DNA
<213> ORGANISM: Legionella pneumophila

<400> SEQUENCE: 49
ggggatacag ctgtttatta tac 23

<210> SEQ ID NO 50
<211> LENGTH: 23
<212> TYPE: DNA
<213> ORGANISM: Legionella pneumophila

<400> SEQUENCE: 50
ggggatacag ctgtttatca tac 23

<210> SEQ ID NO 51
<211> LENGTH: 23
<212> TYPE: DNA
<213> ORGANISM: Legionella pneumophila

<400> SEQUENCE: 51
ggggatacag ctgtttatgt tac 23

<210> SEQ ID NO 52
<211> LENGTH: 23
<212> TYPE: DNA
<213> ORGANISM: Legionella pneumophila

<400> SEQUENCE: 52
ggggatacag ctgtttatgt aac 23

<210> SEQ ID NO 53
<211> LENGTH: 23
<212> TYPE: DNA
<213> ORGANISM: Legionella pneumophila

<400> SEQUENCE: 53
ggggatacag ctgtttatgt gac 23

<210> SEQ ID NO 54
<211> LENGTH: 23
<212> TYPE: DNA
<213> ORGANISM: Legionella pneumophila

<400> SEQUENCE: 54
ggggatttcg ctgtttatga cac 23

<210> SEQ ID NO 55
<211> LENGTH: 23
<212> TYPE: DNA
<213> ORGANISM: Legionella pneumophila

<400> SEQUENCE: 55
ggggatattg ctgtttatga cac 23

<210> SEQ ID NO 56
<211> LENGTH: 23
<212> TYPE: DNA
<213> ORGANISM: Legionella pneumophila

<400> SEQUENCE: 56
ggggatatcg ctgtttatga cac 23

<210> SEQ ID NO 57
<211> LENGTH: 259
<212> TYPE: DNA
<213> ORGANISM: Legionella pneumophila

<400> SEQUENCE: 57
cctgatgtac gtgatggttt aaaaccggtg cataggcgag ttctttttgc gatgagcgag 60
ttgggtaatg attggaataa accttataaa aaatctgctc gtgtagtagg ggatgtcatc 120
ggtaaatacc atcctcacgg ggatacagct gtttatgaca ccattgttcg tatggcccaa 180
cctttttcca tgcgctacct tttaatcgat ggacagggga attttggctc tgtagatgga 240
gatgctccag ctgccatgc 259

<210> SEQ ID NO 58
<211> LENGTH: 22
<212> TYPE: DNA
<213> ORGANISM: Unknown
<220> FEATURE:
<223> OTHER INFORMATION: sense primer

<400> SEQUENCE: 58
cctgatgtac gtgatggttt aa 22

<210> SEQ ID NO 59
<211> LENGTH: 22
<212> TYPE: DNA
<213> ORGANISM: Unknown
<220> FEATURE:
<223> OTHER INFORMATION: antisense primer

<400> SEQUENCE: 59
gcatggcagc tggagcatct cc 22

<210> SEQ ID NO 60
<211> LENGTH: 25
<212> TYPE: DNA
<213> ORGANISM: Unknown
<220> FEATURE:
<223> OTHER INFORMATION: Anchoring probe -continued

```
<400> SEQUENCE: 60

ttgttcgtat ggctcagcct ttttc                                          25


<210> SEQ ID NO 61
<211> LENGTH: 23
<212> TYPE: DNA
<213> ORGANISM: Legionella pneumophila

<400> SEQUENCE: 61

ggggattttg ctgtttatga cac                                            23


<210> SEQ ID NO 62
<211> LENGTH: 8
<212> TYPE: PRT
<213> ORGANISM: Legionella pneumophila

<400> SEQUENCE: 62

Gly Asp Thr Ala Val Tyr Asp Thr
1               5
```